United States Patent
Takato

(12) 
(10) Patent No.: US 10,095,013 B2
(45) Date of Patent: Oct. 9, 2018

(54) OBJECTIVE OPTICAL SYSTEM

(71) Applicant: OLYMPUS CORPORATION, Hachioji-shi, Tokyo (JP)

(72) Inventor: Hideyasu Takato, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/332,140

(22) Filed: Oct. 24, 2016

(65) Prior Publication Data
US 2017/0038570 A1 Feb. 9, 2017

Related U.S. Application Data

(63) Continuation of application No. PCT/JP2015/078571, filed on Oct. 8, 2015.

(30) Foreign Application Priority Data

Nov. 26, 2014 (JP) ................................ 2014-238410

(51) Int. Cl.
*G02B 15/22* (2006.01)
*G02B 13/00* (2006.01)
(Continued)

(52) U.S. Cl.
CPC .......... *G02B 15/22* (2013.01); *A61B 1/00188* (2013.01); *G02B 13/00* (2013.01); *G02B 13/009* (2013.01); *G02B 23/2438* (2013.01)

(58) Field of Classification Search
CPC .. G02B 15/22; G02B 13/009; G02B 23/2438; G02B 13/00; A61B 1/00188
See application file for complete search history.

(56) References Cited

U.S. PATENT DOCUMENTS 4,312,572 A 1/1982 Yamashita et al.
5,469,293 A * 11/1995 Fantone ................. G02B 23/02
359/365
(Continued)

FOREIGN PATENT DOCUMENTS

JP 61044283 B2 10/1986
JP 06317744 A 11/1994
(Continued)

OTHER PUBLICATIONS

International Search Report (ISR) and Written Opinion dated Dec. 8, 2015 issued in International Application No. PCT/JP2015/078571.
(Continued)

*Primary Examiner* — Alicia M Harrington
(74) *Attorney, Agent, or Firm* — Holtz, Holtz & Volek PC

(57) ABSTRACT

An objective optical system includes in order from an object side a first lens group having a positive refractive power, a second lens group having a negative refractive power, and a third lens group having a positive refractive power, wherein focusing is carried out by moving the second lens group with respect to a change in an object-point distance, and the following conditional expressions (2) and (3) are satisfied:

$3 < |\beta|$ (2), and $60° < \omega$ (3), where,

β denotes a lateral magnification of the overall objective optical system at the time of focusing to an object point at a close distance, and ω denotes the maximum half angle of view at the time of focusing to an object point at a long distance.

6 Claims, 17 Drawing Sheets

(51) Int. Cl.
*A61B 1/00* (2006.01)
*G02B 23/24* (2006.01)

(56) References Cited

U.S. PATENT DOCUMENTS

| | | |
|---|---|---|
| 6,252,723 B1 | 6/2001 | Nagaoka |
| 6,433,937 B1 | 8/2002 | Konno |
| 7,160,249 B2 | 1/2007 | Hasegawa |
| 7,267,648 B2 | 9/2007 | Hasegawa |
| 7,499,226 B2 | 3/2009 | Takato |
| 7,511,892 B2 | 3/2009 | Takato |
| 7,927,273 B2 | 4/2011 | Hasegawa |
| 7,982,975 B2 | 7/2011 | Takato |
| 2007/0293725 A1 | 12/2007 | Hasegawa |
| 2008/0004496 A1 | 1/2008 | Hasegawa |
| 2015/0378137 A1 | 12/2015 | Obikane |

FOREIGN PATENT DOCUMENTS

| | | |
|---|---|---|
| JP | 11316339 A | 11/1999 |
| JP | 2000267002 A | 9/2000 |
| JP | 2004313769 A | 11/2004 |
| JP | 2004313772 A | 11/2004 |
| JP | 2007233036 A | 9/2007 |
| JP | 2007260305 A | 10/2007 |
| JP | 2009294496 A | 12/2009 |
| JP | 2015075508 A | 4/2015 |

OTHER PUBLICATIONS

International Preliminary Report on Patentability and Written Opinion (and English translation thereof) dated Jun. 8, 2017, issued in International Application No. PCT/JP2015/078571.

\* cited by examiner

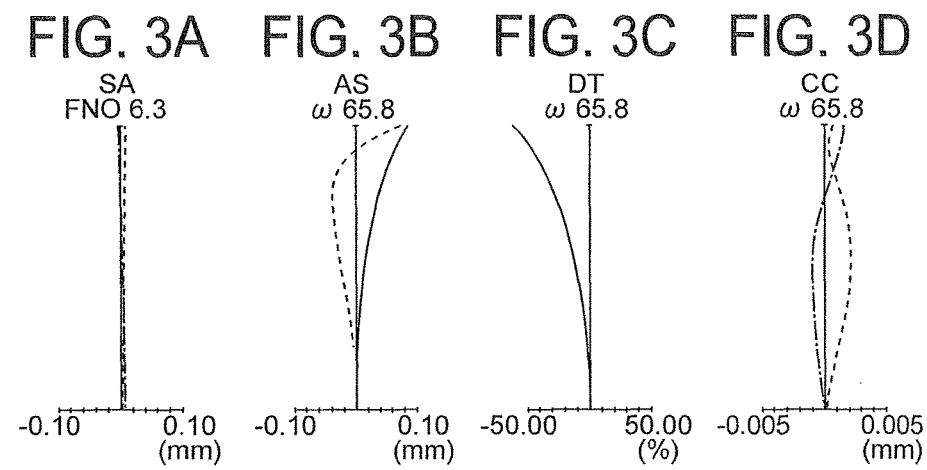

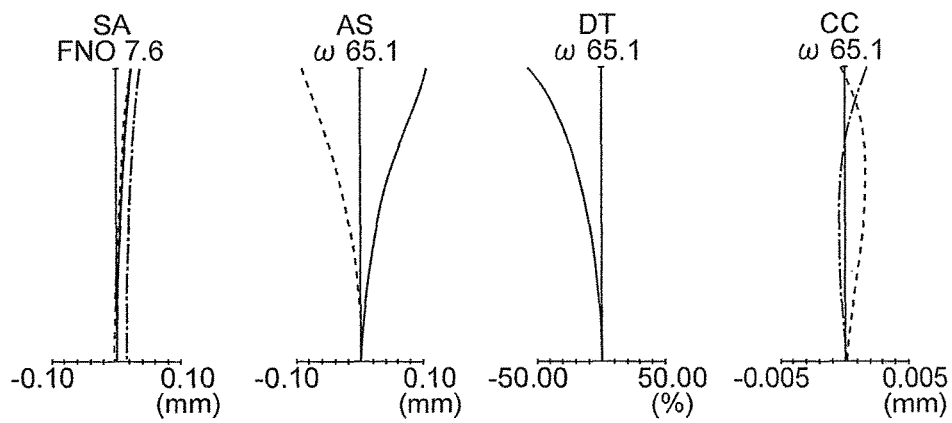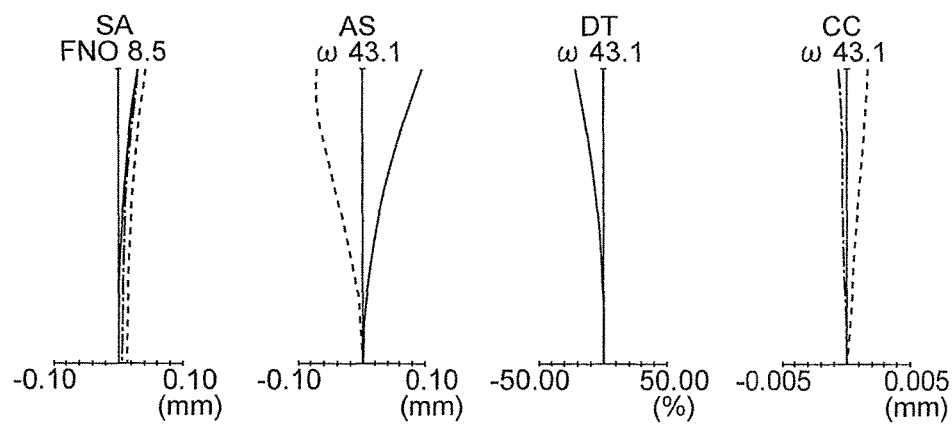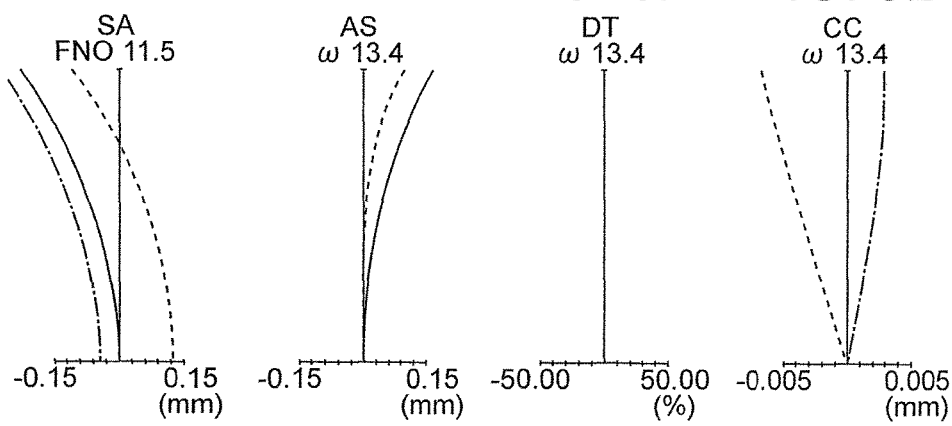

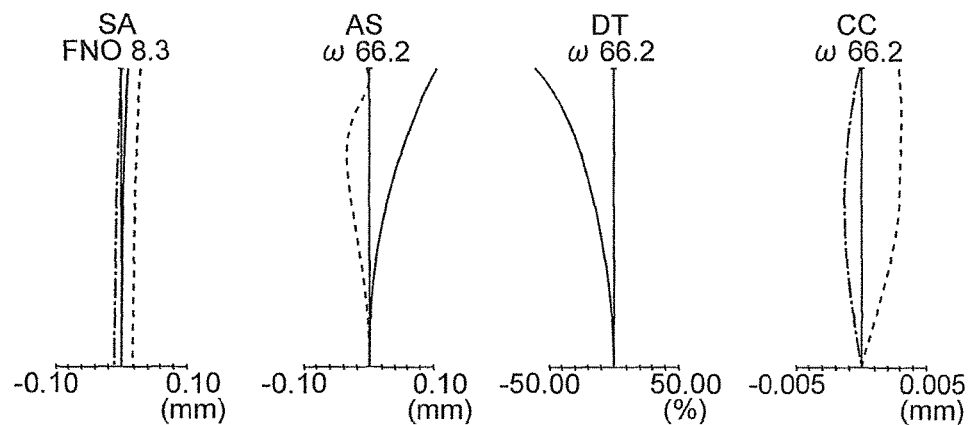
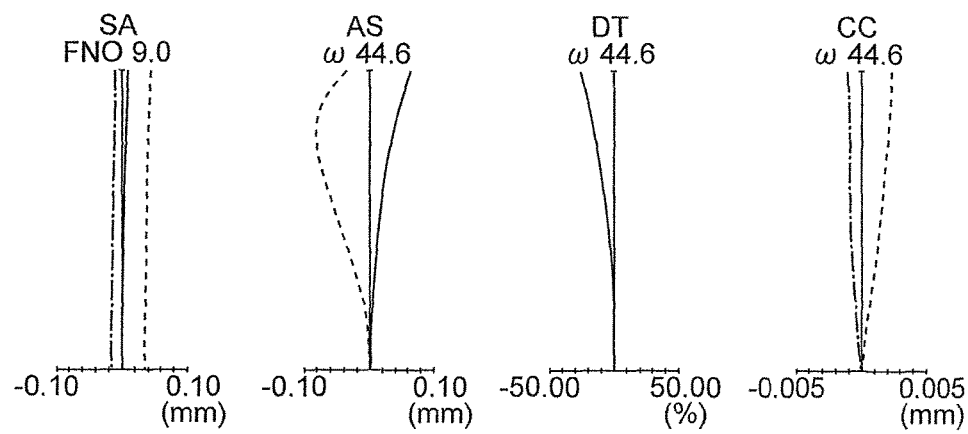
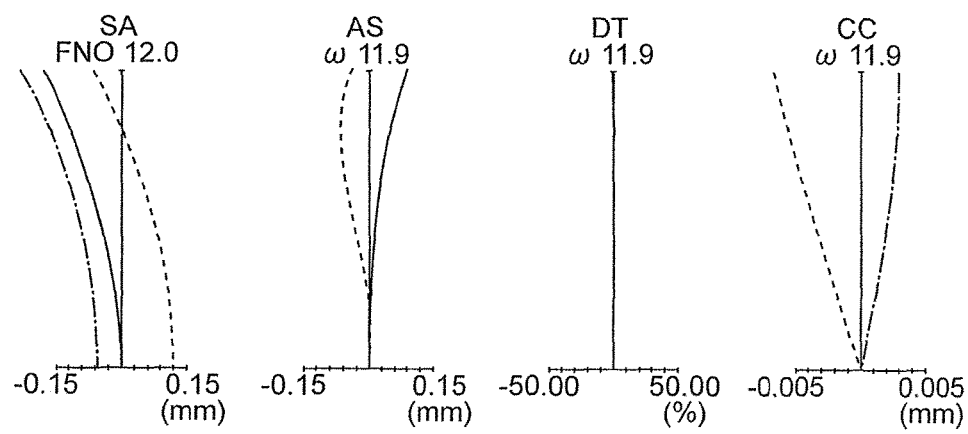

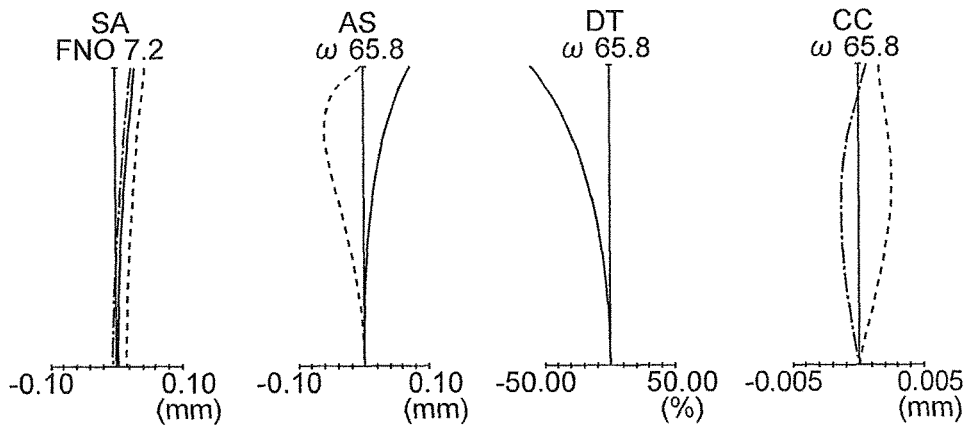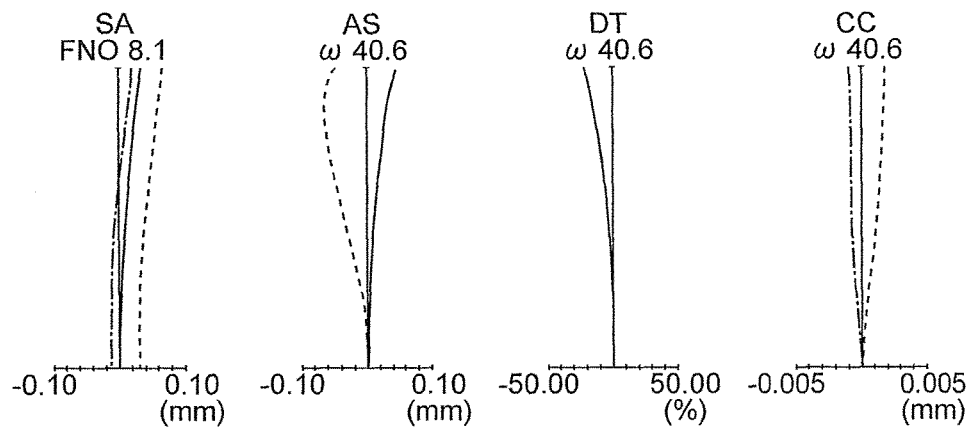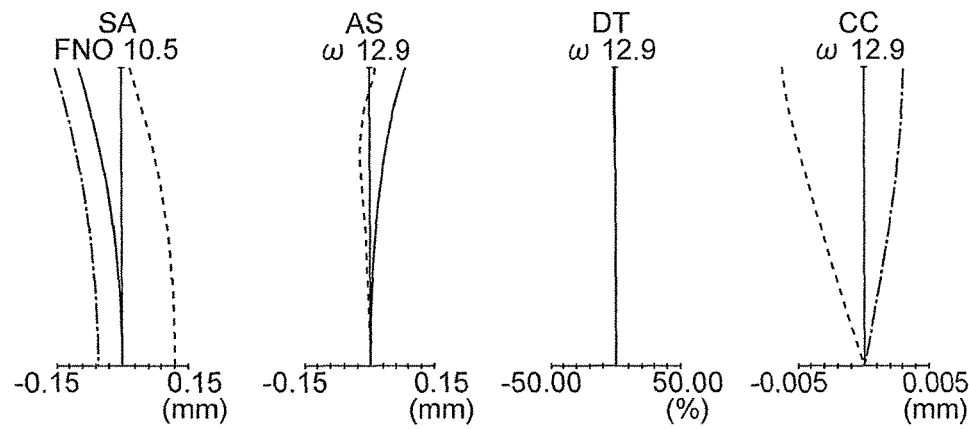

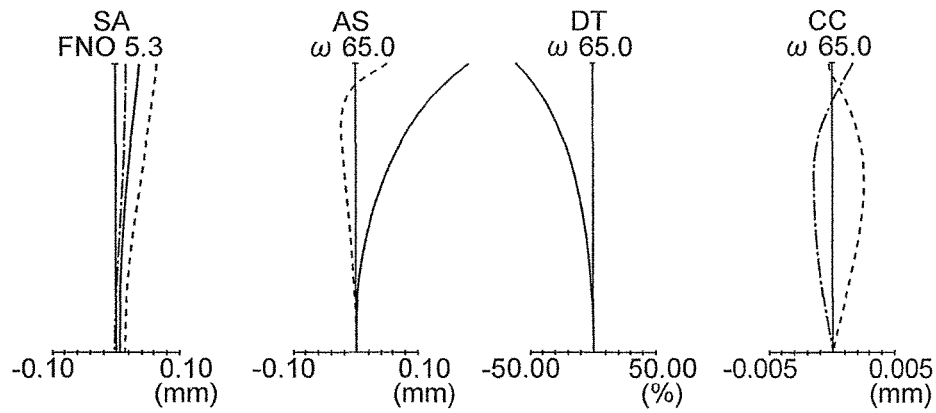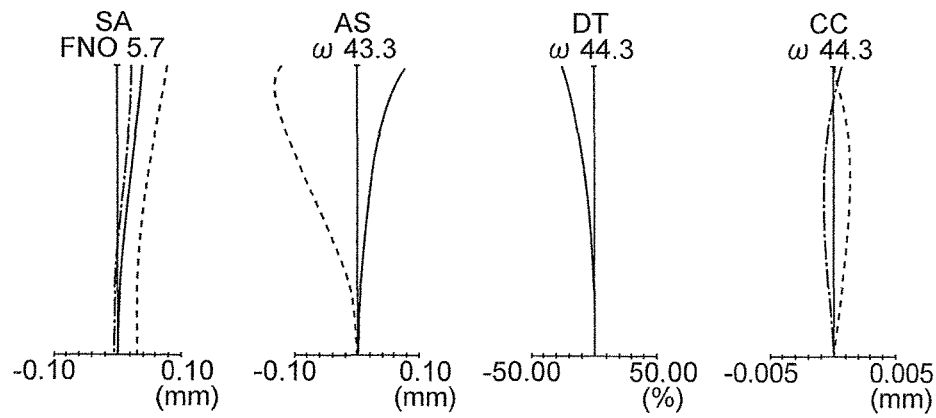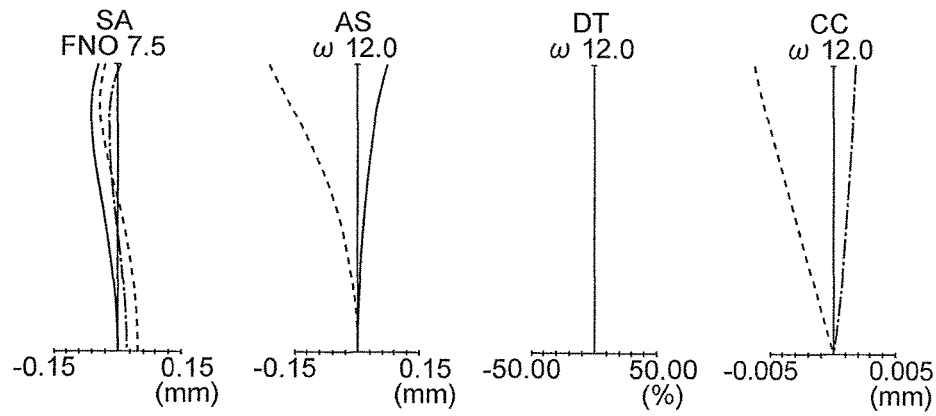

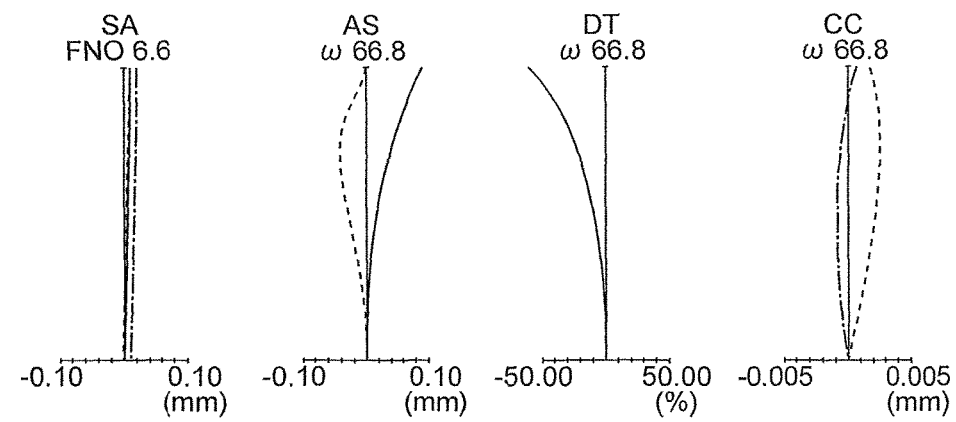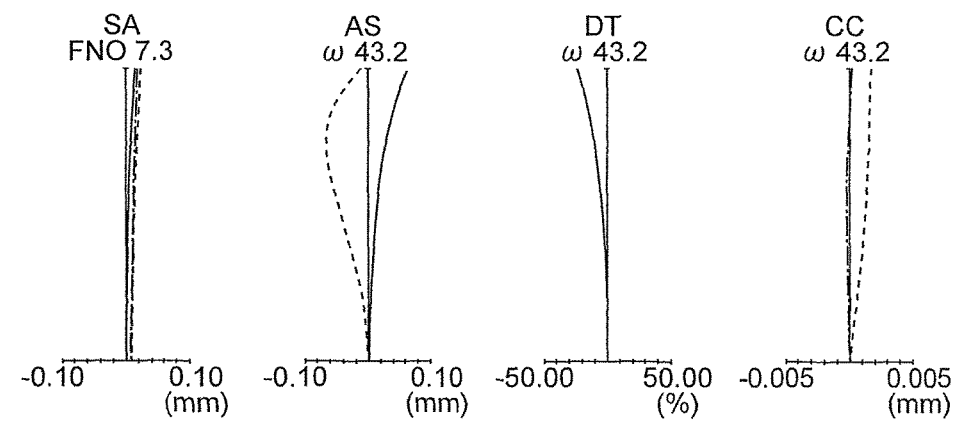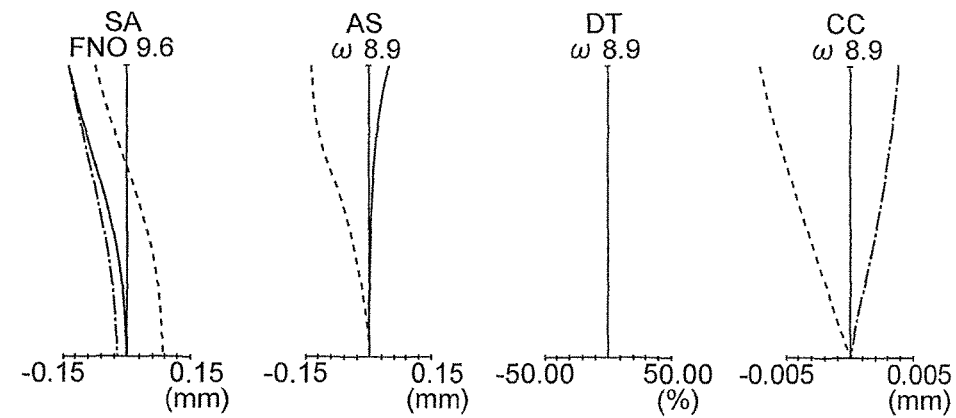

OBJECTIVE OPTICAL SYSTEM

CROSS-REFERENCE TO RELATED APPLICATION

The present application is a continuation application of PCT/JP2015/078571 filed on Oct. 8, 2015 which is based upon and claims the benefit of priority from Japanese Patent Application No. 2014-238410 filed on Nov. 26, 2014; the entire contents of which are incorporated herein by reference.

BACKGROUND OF THE INVENTION

Field of the Invention

The present invention relates to an objective optical system having a focusing function, and in particular, to an objective optical system for endoscope that enables a proximity magnifying observation, an objective optical system of a digital camera and a video camera that enables macro photography or an objective optical system of a miniature camera for consumer use.

Description of the Related Art

In a field of medical endoscopes, precise diagnosis of a lesioned part has been carried out by an observation through an endoscope (hereinafter, referred to as 'endoscopic observation'). Therefore, an objective lens of an endoscope, in a state of being close to a lesioned part, is sought to enable magnifying observation of the lesioned part. As such objective lens, an objective lens in which it is possible to change an object-point distance (object distance) at which the focusing can be done (hereinafter, referred to as 'magnifying endoscope objective lens'), is available.

In the magnifying endoscope objective lens, by focusing to an object point at a close distance, it is possible to carry out proximity magnifying observation. Moreover, it is possible to carry out normal observation by focusing to an object point at a long distance. The normal observation is an observation with a magnification lower than a magnification in the proximity magnifying observation. In the normal observation, it is possible to observe a wide range including a lesioned part and a surrounding portion thereof. As the magnifying endoscope objective lens, magnifying endoscope objective lenses disclosed in Japanese Patent Publication after Examination No. Sho 61-044283, Japanese Patent Application Laid-open Publication Nos. Hei 06-317744, Hei 11-316339 and 2000-267002 are available.

The magnifying endoscope objective lenses disclosed in Japanese Patent Publication after Examination No. Sho 61-044283, Japanese Patent Application Laid-open Publication Nos. Hei 06-317744 and Hei 11-316339 include a first lens group having a positive refractive power, a second lens group having a negative refractive power, and a third lens group having a positive refractive power. At the time of focusing to an object point at a close distance and an object point at a long distance, the second lens group having a negative refractive power moves.

The magnifying endoscope objective lens disclosed in Japanese Patent Application Laid-open Publication No. 2000-267002 includes a first lens group having a negative refractive power, a second lens group having a positive refractive power, and a third lens group having a negative refractive power. At the time of focusing to an object point at a close distance and an object point at a long distance, the second lens group having a positive refractive power moves.

In recent years, for improving an accuracy of diagnosis, a high quality of an endoscope image has been sought. In order to meet the requirement, a use of an image pickup element with number of pixels larger than the number of pixels of a conventional image pickup element has been started. Consequently, the magnifying endoscope objective lens is sought to have a high resolving power.

Moreover, in precise diagnosis of a lesioned part in recent years, it has been strongly sought that an observation of same level as an observation through a microscope (hereinafter, referred to as 'microscopic observation') be carried out even by the endoscopic observation. The observation of same level as the microscopic observation means an observation with about same degree of magnification and resolving power. For this, the magnifying endoscope objective lens is sought to have even larger magnification at the time of proximity magnifying observation. By doing so, an observation of same level as the microscopic observation is possible even by an endoscope.

In endoscopic observation, observation of a physiological tissue with the same level as the microscopic observation, such as an observation at the cellular level, has heretofore been difficult. Consequently, the only method available was to extract a part of a physiological tissue by biopsy after a lesioned part has been identified by endoscopic observation, and to observe the extracted physiological tissue by a microscope. However, by using a magnifying endoscope objective lens having a large magnification, there is a merit of being able to observe a physiological tissue with the same level as the microscopic observation while being in-vivo, as an extension of the normal observation.

As an endoscope objective lens which enables observation of the same level as the microscopic observation, endoscope objective lenses disclosed in Japanese Patent Application Laid-open Publication Nos. 2004-313769, 2004-313772, 2007-233036, 2007-260305 and 2009-294496 are available.

The endoscope objective lenses disclosed in Japanese Patent Application Laid-open Publication Nos. 2004-313769 and 2004-313772 are single focal length endoscope objective lenses. A single focal length endoscope objective lens is an objective lens in which an object-point distance to which the focusing can be done has been determined in advance. Therefore, the endoscope objective lenses disclosed in Japanese Patent Application Laid-open Publication Nos. 2004-313769 and 2004-313772 do not include a lens group that moves.

The endoscope objective lenses disclosed in Japanese Patent Application Laid-open Publication Nos. 2007-233036, 2007-260305 and 2009-294496 are magnifying endoscope objective lenses.

Two magnifying endoscope objective lenses have been disclosed in Japanese Patent Application Laid-open Publication No. 2007-233036. One magnifying endoscope objective lens includes a first lens group having a positive refractive power, a second lens group having a negative refractive power, and a third lens group having a positive refractive power. At the time of focusing to an object point at a close distance or an object point at a long distance, the second lens group having a negative refractive power moves. Moreover, the other magnifying endoscope objective lens includes a first lens group having a negative refractive power, a second lens group having a positive refractive power, and a third lens group having a positive refractive power. At the time of focusing to an object point at a close distance and an object point at a long distance, the second lens group having a positive refractive power moves.

The magnifying endoscope objective lens disclosed in Japanese Patent Application Laid-open Publication No.

2007-260305 includes four lens groups. At the time of focusing to an object point at a close distance and an object point at a long distance, a second lens group and a third lens group move, or the third lens group moves.

The magnifying endoscope objective lens disclosed in Japanese Patent Application Laid-open Publication No. 2009-294496 includes a first lens group having a positive refractive power, a second lens group having a negative refractive power, and a third lens group having a positive refractive power. At the time of focusing to an object point at a close distance and an object point at a long distance, the second lens group having a negative refractive power moves.

Moreover, a desire to carry out the proximity magnification observation with a high resolving power and enlarge magnification is there not only in endoscopes, but also in digital cameras and video cameras. The macro photography in digital cameras and video cameras corresponds to the proximity magnifying observation. Therefore, even in optical systems of digital cameras and video cameras, high magnification and high resolving power in the macro photography have been sought. Moreover, in optical systems of digital cameras and video cameras, small-sizing of an optical system is desired.

SUMMARY OF THE INVENTION

An objective optical system according to an aspect of the present invention comprises in order from an object side;

a first lens group having a positive refractive power, a second lens group having a negative refractive power, and a third lens group having a positive refractive power, wherein focusing is carried out by moving the second lens group with respect to a change in an object-point distance, and the following conditional expressions (2) and (3) are satisfied:

$$3 < |\beta| \quad (2), \text{ and}$$

$$60° < \omega \quad (3),$$

where,

β denotes a lateral magnification of the overall objective optical system at a time of focusing to an object point at a close distance, and ω denotes a maximum half angle of view at the time of focusing to an object point at a long distance.

Moreover, an objective optical system according to another aspect of the present invention comprises in order from an object side;

a first lens group having a positive refractive power, a second lens group having a negative refractive power, and a third lens group having a positive refractive power, wherein focusing is carried out by moving only the second lens group with respect to a change in an object-point distance, and the first lens group includes at least one negative lens, two cemented lenses, and one positive lens, and the negative lens is disposed nearest to an object, and the cemented lens includes a positive lens and a negative lens.

Moreover, an objective optical system according to a preferable aspect of the present invention is to be used for an endoscope.

BRIEF DESCRIPTION OF THE DRAWINGS

FIG. 2A is a cross-sectional view in a normal observation state, FIG. 2B is a cross-sectional view in an intermediate state, and FIG. 2C is a cross-sectional view in a proximity magnifying observation state;

FIG. 3A, FIG. 3B, FIG. 3C, FIG. 3D, FIG. 3E, FIG. 3F, FIG. 3G, FIG. 3H, FIG. 3I, FIG. 3J, FIG. 3K, and FIG. 3L are aberrations diagrams showing a spherical aberration (SA), an astigmatism (AS), a distortion (DT), and a chromatic aberration of magnification (CC) of the example 1;

FIG. 4A is a cross-sectional view in a normal observation state, FIG. 4B is a cross-sectional view in an intermediate state, and FIG. 4C is a cross-sectional view in a proximity magnifying observation state;

FIG. 5A, FIG. 5B, FIG. 5C, FIG. 5D, FIG. 5E, FIG. 5F, FIG. 5G, FIG. 5H, FIG. 5I, FIG. 5J, FIG. 5K, and FIG. 5L are aberration diagrams showing a spherical aberration (SA), an astigmatism (AS), a distortion (DT), and a chromatic aberration of magnification (CC) of the example 2;

FIG. 6A is a cross-sectional view in a normal observation state, FIG. 6B is a cross-sectional view in an intermediate state, and FIG. 6C is a cross-sectional view in a proximity magnifying observation state;

FIG. 7A, FIG. 7B, FIG. 7C, FIG. 7D, FIG. 7E, FIG. 7F, FIG. 7G, FIG. 7H, FIG. 7I, FIG. 7J, FIG. 7K, and FIG. 7L are aberration diagrams showing a spherical aberration (SA), an astigmatism (AS), a distortion (DT), and a chromatic aberration of magnification (CC) of the example 3;

FIG. 8A is a cross-sectional view in a normal observation state, FIG. 8B is a cross-sectional view in an intermediate state, and FIG. 8C is a cross-sectional view in a proximity magnifying observation state;

FIG. 9A, FIG. 9B, FIG. 9C, FIG. 9D, FIG. 9E, FIG. 9F, FIG. 9G, FIG. 9H, FIG. 9I, FIG. 9J, FIG. 9K, and FIG. 9L are aberration diagrams showing a spherical aberration (SA), an astigmatism (AS), a distortion (DT), and a chromatic aberration of magnification (CC) of the example 4;

FIG. 10A is a cross-sectional view in a normal observation state, FIG. 10B is a cross-sectional view in an intermediate state, and FIG. 10C is a cross-sectional view in a proximity magnifying observation state;

FIG. 11A, FIG. 11B, FIG. 11C, FIG. 11D, FIG. 11E, FIG. 11F, FIG. 11G, FIG. 11H, FIG. 11I, FIG. 11J, FIG. 11K, and FIG. 11L are aberration diagrams showing a spherical aberration (SA), an astigmatism (AS), a distortion (DT), and a chromatic aberration of magnification (CC) of the example 5;

FIG. 12A is a cross-sectional view in a normal observation state, FIG. 12B is a cross-sectional view in an intermediate state, and FIG. 12C is a cross-sectional view in a proximity magnifying observation state;

FIG. 13A, FIG. 13B, FIG. 13C, FIG. 13D, FIG. 13E, FIG. 13F, FIG. 13G, FIG. 13H, FIG. 13I, FIG. 13J, FIG. 13K, and FIG. 13L are aberration diagrams showing a spherical aberration (SA), an astigmatism (AS), a distortion (DT), and a chromatic aberration of magnification (CC) of the example 6;

FIG. 14A is a cross-sectional view in a normal observation state, FIG. 14B is a cross-sectional view in an intermediate state, and FIG. 14C is a cross-sectional view in a proximity magnifying observation state;

FIG. 16A is a cross-sectional view in a normal observation state, FIG. 16B is a cross-sectional view in an intermediate state, and FIG. 16C is a cross-sectional view in a proximity magnifying observation state.

DETAILED DESCRIPTION OF THE INVENTION

Reasons for adopting such arrangements and effects thereof in an objective optical system according to the present embodiment will be described below by referring to the accompanying diagrams. However, the present invention is not limited to the following embodiments.

The objective optical system according to the present embodiment can be used for an objective lens of an endoscope. In this case, the objective optical system according to present embodiment, in endoscopic observation, enables to carry out normal observation and proximity magnifying observation with one optical system. For this, the objective optical system includes a plurality of lens groups, and at least one of the plurality of lens groups moves on an optical axis. Accordingly, it is possible to carry out the normal observation when focused to an object point at a long distance and the proximity magnifying observation when focused to an object point at a close distance. In other words, an observation of same level as microscopic observation in the form of an extension of the proximity magnifying observation, and proximity magnifying observation with even higher magnification are possible.

A basic arrangement of the objective optical system according to the present embodiment will be described below. In the basic arrangement, the objective optical system includes in order from an object side, a first lens group having a positive refractive power, a second lens group having a negative refractive power, and a third lens group having a positive refractive power. Moreover, focusing is carried out by moving the second lens group with respect to a change in an object-point distance.

The first lens group includes a single lens and a cemented lens. In the first lens group, at least one negative lens is to be used as the single lens. The negative lens is to be disposed nearest to an object. Moreover, in the first lens group, at least two cemented lenses are to be used as a cemented lens. In such manner, the first lens group includes at least one negative lens and two cemented lenses.

In the first lens group, additionally one positive lens or two positive lenses may be used as a single lens. Moreover, in the first lens group, additionally one cemented lens may be used as the cemented lens.

The second lens group includes one cemented lens. In the second lens group, additionally one negative lens may be used.

The third lens group includes either only a single lens or a single lens and a cemented lens. The third lens group may include at the most three single lenses as the single lens. Moreover, in the third lens group, one cemented lens is used as the cemented lens.

Figure 1:
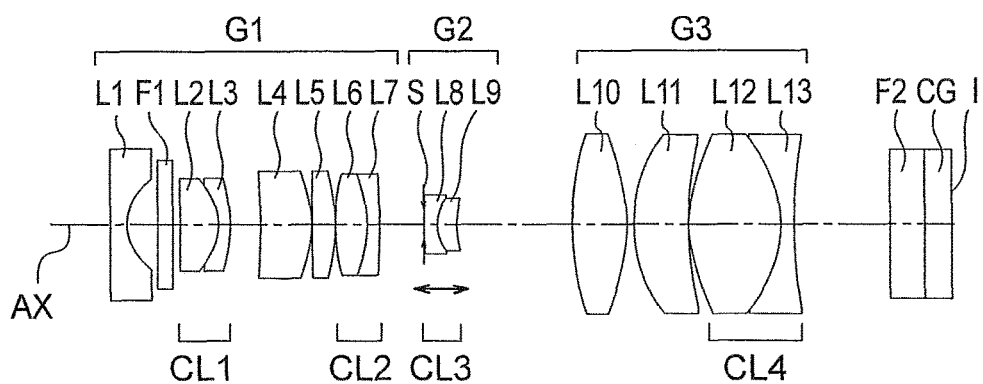
FIG. 1 is a diagram showing a cross-sectional arrangement of an objective optical system according to an embodiment of the present invention.

A specific arrangement of the objective optical system according to the present embodiment will be described below. FIG. 1 is a diagram showing a cross-sectional arrangement of the objective optical system according to the present embodiment.

A first lens group G1 includes in order from an object side, a negative lens L1, a cemented lens CL1, a positive lens L4, a positive lens L5, and a cemented lens CL2. Here, the cemented lens CL1 includes a positive lens L2 and a negative lens L3. The cemented lens CL2 includes a positive lens L6 and a negative lens L7.

If a single lens is let to be a unit, the first lens group G1 includes seven single lenses. A second lens from the object side becomes the positive lens L2 and a fourth lens from the object side becomes the positive lens L4.

Whereas, if a lens component is let to be a unit, the first lens group G1 includes five lens components. A second lens component from the object side becomes the cemented lens CL1 and a fourth lens component from the object side becomes the positive lens L6. Here, a lens component means a single lens or a cemented lens.

A second lens group G2 includes a cemented lens CL3. The cemented lens CL3 includes a negative lens L8 and a positive lens L9.

Moreover, the second lens group G2 has an aperture stop S on the object side. By disposing the aperture stop S near the second lens group G2, it is possible to make low a height of a light ray that passes through the second lens group G2. As a result, it is possible to make an outer diameter of the second lens group G2 small.

The second lens group G2 moves at the time of focusing. By the second lens group G2 moving, the focusing can be carried out even when an object point is positioned anywhere from a long distance up to a close distance. It is possible to carry out normal observation when focused to an object point at a long distance, and proximity magnifying observation when focused to an object point at a close distance.

FIG. 1 is a diagram in a state in which the object point is positioned between the long distance and the close distance, or other words, in an intermediate state. In a case of focusing to the object point positioned at the long distance, the second lens group G2 moves from the position in FIG. 1 toward the object side. In a case of focusing to the object point positioned at the close distance, the second lens group moves from the position in FIG. 1 toward an image side.

A moving mechanism is necessary for moving the second lens group G2 in an optical axial direction. As mentioned above, in the objective optical system according to the present embodiment, since it is possible make the second lens group G2 small-sized, it is possible to dispose easily the moving mechanism around the second lens group G2.

Moreover, since the number of lens groups that move is one, it is possible to make the moving lens group light-weight. Consequently, it is possible to reduce a load applied on the moving mechanism. Furthermore, it is possible to make the moving mechanism simple.

As the moving mechanism, for example, an actuator is available. The actuator is to be connected to a lens frame holding the second lens group G2, and accordingly a drive force is imparted to the lens frame.

A third lens group G3 includes a positive lens L10, a positive lens L11, and a cemented lens CL4. The cemented lens CL4 includes a positive lens L12 and a negative lens L13.

In the objective optical system according to the present embodiment, a plane-parallel plate F1 is disposed in the first lens group G1. The plane-parallel plate F1 is a filter for cutting light of a specific wavelength such as laser light of YAG laser (light of wavelength 1060 nm), laser light of semiconductor laser (light of wavelength 810 nm), or light of wavelength of near-infrared region. The plane-parallel plate F1 may be disposed in the second lens group G2, or in the third lens group G3, or on the image side of the third lens group G3.

Moreover, a plane-parallel plate F2 and a cover glass CG are disposed on the image side of the third lens group G3. The cover glass CG is provided to an image pickup element for protecting an image pickup surface of the image pickup element. Since an image-side surface of the cover glass CG is an image plane I of the objective optical system, the image pickup element is disposed such that the image plane I and the image pickup surface coincide. An image pickup optical system is formed by the objective optical system and the image pickup element.

The objective optical system according to a first embodiment has the abovementioned basic arrangement, and the following conditional expression (1) is satisfied:

$$0 < f_f/f_e < 0.33 \quad (1),$$

where, $f_f$ denotes a front focal position at a time of focusing to an object point at a close distance, and $f_e$ denotes a focal length of the overall objective optical system at the time of focusing to the object point at the close distance.

Conditional expression (1) is related to the front focal position of the objective optical system at the time of focusing to the object point at the close distance, and is necessary for making large the magnification at the time of proximity magnifying observation. Here, $f_f$ denotes a distance from a lens surface nearest to an object of the objective optical system up to the front focal position.

The object-point distance is a distance from the lens surface nearest to the object of the objective optical system up to an object point (an object to be observed). For making large the magnification at the time of the proximity magnifying observation by shortening the object-point distance, it is preferable to bring the front focal position as close as possible to the objective optical system. When the front focal position is separated apart from the objective optical system, the objective optical system cannot come closer to the object point by distance separated apart. Therefore, by making large the magnification at the time of the proximity magnifying observation, it is necessary to make small a distance from the front focal position up to the objective optical system.

When exceeding an upper limit value of conditional expression (1), the front focal position is separated excessively apart from the objective optical system. Consequently, at the time of the proximity magnifying observation, desired magnification cannot be achieved. Therefore, it is not preferable to exceed the upper limit value of conditional expression (1).

When falling below a lower limit value of conditional expression (1), the front focal position approaches excessively closer to the objective optical system. In this case, an object-side surface of the first lens L1 has to be made a concave surface. However, in a case of using the objective optical system in an endoscope, it is preferable that the object-side surface of the first lens L1 is either a convex surface or a flat surface. Therefore, it is not preferable to let the object-side surface of the first lens L1 to be the concave surface, or in other words, to fall below the lower limit value of conditional expression (1).

An objective optical system according to a second embodiment has the abovementioned basic arrangement, and the following conditional expressions (2) and (3) are satisfied:

$$3 < |\beta| \quad (2), \text{ and}$$

$$60° < \omega \quad (3),$$

where, $\beta$ denotes a lateral magnification of the overall objective optical system at the time of focusing to an object point at a close distance, and $\omega$ denotes a maximum half angle of view at the time of focusing to an object point at a long distance.

By observing a lesion occurred in a physiological tissue at a cellular level, it is possible to observe a phenomenon that appears specifically (hereinafter, referred to as 'specific phenomenon') when a healthy cell becomes cancerous for example. Specific phenomena include a disarray of cell arrangement, an abnormal thickening of cell nucleus, and an abnormal growth of capillary blood vessels surrounding a cell nucleus. For observing such specific phenomenon, at the time of the proximity magnifying observation, it is necessary to secure a magnification of same level as a microscopic observation. Moreover, it becomes indispensable to secure a resolving power of same level as the microscopic observation in a range from a few tens of $\mu m^2$ to approximately 100 $\mu m^2$ within a field of view.

In a case in which the objective optical system of the present embodiment is combined with an image pickup element in which the number of pixels is made large, since the objective optical system of the present embodiment satisfies conditional expression (2), the resolving power of a few $\mu m$ up to approximately 10 $\mu m$ is achieved. Taking into consideration a case of observing by displaying an image on a 19 inch monitor, since magnification of about 400 times to 600 times can be achieved, the observation at the cellular level, and furthermore, the observation at a cell-nucleus level become possible. Accordingly, it is possible to observe the specific phenomenon accurately.

In a case in which the magnification at the time of the proximity magnifying observation is large, an extremely narrow range is to be observed with a high magnification. Therefore, in the proximity magnifying observation, it is desirable to observe by dabbing a front-end portion of an insertion portion at the physiological tissue. By doing so, the objective optical system makes a contact with and is fixed to a site to be observed. Accordingly, since it is possible to prevent shaking, a stable image is achieved.

In a case of not satisfying conditional expression (2), the magnification at the time of the proximity magnifying observation is inadequate. Compensating the inadequate magnification by using an electrical compensating means such as an electronic zoom may be taken in to consideration. However, if an image before carrying out the electronic zoom is not an image with an extremely small aberration, quality of image after carrying out the electronic zoom is degraded. An image with a degraded quality is not preferable as an image to be used for diagnosis of the lesion.

Moreover, in the objective optical system according to the present embodiment, at the time of the proximity magnifying observation, observation of same level as the microscopic observation is possible. However, since it is necessary to carry out screening of inside of the body for finding a lesioned part, and moreover, to treat the lesioned part, it is necessary to secure a wide field of view at the time of normal observation.

By satisfying conditional expression (3), it is possible to secure the wide field of view at the time of the normal observation. The field of view in this case is a field of view of same degree as of an objective optical system without the function of the proximity magnifying observation. Thus, by satisfying conditional expression (3), even with the objective optical system that enables the proximity magnifying observation, it is possible to secure a sufficiently wide field of view at the time of the normal observation. Consequently, it is possible to carry out screening, diagnosis, and treatment without any problem.

An objective optical system according to a third embodiment has the abovementioned basic arrangement, and in which only the second lens group is to be moved, and the first lens group includes at least one negative lens, two cemented lenses, and one positive lens, and the negative lens is disposed nearest to an object, and the cemented lens includes a positive lens and a negative lens.

The objective optical system according to the present embodiment, similarly as the objective optical system according to the first embodiment and the objective optical system according to the second embodiment, includes a first lens group having a positive refractive power, a second lens group having a negative refractive power, and a third lens group having a positive refractive power, and focusing is carried out by moving only the second lens group with respect to a change in an object-point distance.

In such objective optical system, it is desired that the first lens group is formed by combining two cemented lenses and one positive lens. By using two cemented lenses, it is possible to correct a chromatic aberration adequately.

Particularly, at the time of carrying out proximity magnifying observation, it is desired that an imaging performance of a lens group positioned on an object side of an aperture stop, or in other words, an imaging performance of the first lens group is favorable. In the proximity magnifying observation, enlarge magnification by a lens group positioned on the image side of the aperture stop is large. Therefore, it is necessary to correct favorably a longitudinal chromatic aberration in particular, in the first lens group. When a cemented lens is not disposed in the first lens group, chromatic blurring occurred in an image is spread largely at the time of the proximity magnifying observation. Therefore, it is not preferable not to dispose a cemented lens in the first lens group.

Moreover, by using one positive lens, a part of the positive refractive power in the first lens group is imposed on the positive lens. For dispersing the positive refractive power in the first lens group, it is preferable to add one positive lens in the first lens group. By doing so, it is possible to suppress an occurrence of aberration.

Moreover, in the objective optical systems according to the first embodiment to the third embodiment (hereinafter, referred to as 'objective optical systems according to the present embodiment'), it is desirable that the following conditional expressions (4) and (5) are satisfied:

$$-2 < f_{G12w}/f_w < -1 \quad (4), \text{ and}$$

$$0.5 < f_{G12e}/f_e < 1.62 \quad (5),$$

where, $f_{G12w}$ denotes a combined focal length of the first lens group and the second lens group at the time of focusing to the object point at the long distance, $f_{G12e}$ denotes a combined focal length of the first lens group and the second lens group at the time of focusing to the object point the a close distance, $f_e$ denotes a focal length of the overall objective optical system at the time of focusing to then object point at the long distance, and $f_w$ denotes the focal length of the overall objective optical system at the time of focusing to the object point at the close distance.

Conditional expression (4) is related to the combined focal length of the first lens group and the second lens group at the time of normal observation. By satisfying conditional expression (4), it is possible to correct an astigmatism favorably.

When falling below a lower limit value of conditional expression (4), a meridional image plane is substantially inclined toward a minus side. When exceeding an upper limit value of conditional expression (4), both the meridional image plane and a sagittal image plane are inclined toward a plus side. Therefore, exceeding the upper limit value of conditional expression (4) is not preferable.

Conditional expression (5) is related to the astigmatism at the time of proximity magnifying observation and the magnification of the overall optical system. By satisfying conditional expression (5), it is possible to correct the astigmatism at the time of the proximity magnifying observation as well as to secure the magnification necessary as the optical system as a whole.

When falling below a lower limit value of conditional expression (5), at the time of the proximity magnifying observation, since the meridional image plane is inclined toward the minus side and the sagittal image plane is inclined toward the plus side, there is an increase in the astigmatism. Therefore, falling below the lower limit value of conditional expression (5) is not preferable.

When exceeding an upper limit value of conditional expression (5), although there is no deterioration of astigmatism, the magnification that is necessary for the optical system as a whole becomes low. Consequently, the desired magnification cannot be achieved in both the normal observation and the proximity magnifying observation. Therefore, exceeding the upper limit value of conditional expression (5) is not preferable.

Furthermore, it is desirable that the following conditional expression (5') is satisfied instead of conditional expression (5):

$$0.5 < f_{G12e}/f_e < 1.38 \quad (5').$$

By satisfying conditional expression (5'), it is possible to correct more favorably the astigmatism at the time of the proximity magnifying observation as well as to secure adequately the magnification necessary for the optical system as a whole.

Moreover, in the objective optical system according to the present embodiment, it is preferable that the following conditional expression (6) is satisfied:

$$1.81 < f_{G1L2}/f_w < 3.85 \quad (6),$$

where, $f_{G1L2}$ denotes a focal length of a lens alone, positioned second from the object side in the first lens group, and $f_w$ denotes the focal length of the overall objective optical system at the time of focusing to the object point at the long distance.

In the objective optical system according to the present embodiment, a negative lens is disposed first and a positive lens is disposed second when counted from the object side. Such arrangement of the lenses exerts an effect of suppressing a fluctuation in a curvature of field at the time of the normal observation as well as the proximity magnifying observation.

Moreover, with such lens arrangement, it is preferable that conditional expression (6) is satisfied. By satisfying conditional expression (6), it is possible to suppress further the fluctuation in the curvature of field at the time of the normal observation as well as the proximity magnifying observation.

When falling below a lower limit value of conditional expression (6), the image plane at the time of the normal observation is inclined toward the plus side, and the image plane at the time of the proximity magnifying observation is inclined toward the minus side. When exceeding an upper limit value of conditional expression (6), the image plane at the time of the normal observation is inclined toward the minus side and the image plane at the time of the proximity magnifying observation is inclined toward the plus side. Even when the positive lens is a single lens, it may be cemented with a negative lens positioned on the image side.

Moreover, in the objective optical system according to the present embodiment, it is preferable that the following conditional expression (7) is satisfied:

$$0.9 < HF/f_e < 1.33 \quad (7),$$

where,

HF denotes a front principal-point position at the time of focusing to the object point at the close distance, and $f_e$ denotes the focal length of the overall objective optical system at the time of focusing to the object point at the close distance.

Conditional expression (7) is related to the front principal-point position at the time of focusing to the object point at the close distance. By satisfying conditional expression (7), it is possible to secure the magnification necessary for the proximity magnifying observation. Here, HF is a distance from a lens surface nearest to object of the objective optical system up to the front principal-point position.

When falling below a lower limit value of conditional expression (7), although the magnification at the time of the proximity magnifying observation becomes large, it is necessary to make large a refractive power of an image-side surface of the negative lens disposed nearest to the object. Since the refractive power of the first lens group is a positive refractive power, for maintaining the positive refractive power of each lens in the first lens group, there arises a need to make large the refractive power of the positive lens in particular. Consequently, from the normal observation up to the proximity magnifying observation, a spherical aberration and the curvature of field become large. Therefore, falling below the lower limit value of conditional expression (7) is not preferable.

When exceeding an upper limit value of conditional expression (7), it becomes difficult to increase the magnification at the time of the proximity magnifying observation to the desired magnification.

Moreover, in the objective optical system according to the present embodiment, it is desirable that the following conditional expression (8) is satisfied:

$$2.5 < f_{G1L4}/f_w < 10.5 \quad (8),$$

where, $f_{G1L4}$ denotes a focal length of a lens component positioned fourth from the object side in the first lens group, and $f_w$ denotes the focal length of the overall objective optical system at the time of focusing to the object point at the long distance, and here the lens component is either a single lens or a cemented lens.

Conditional expression (8) is related to the focal length of the lens component positioned fourth from the object side, out of the lens components in the first lens group. Here, the lens component means either a single lens or a cemented lens.

The lens component positioned fourth from the object side may be a single lens or may be a cemented lens, and in either of the cases, the lens component positioned fourth from the object side has a positive refractive power and is involved in correction of a chromatic aberration of magnification. By satisfying conditional expression (8), it is possible to correct the chromatic aberration of magnification favorably.

When falling below a lower limit value of conditional expression (8), the chromatic aberration of magnification of higher-order about an F-line and a g-line, and particularly the chromatic aberration of magnification of higher-order about the g-line occurs substantially on the minus side, and the chromatic aberration of magnification of higher-order about a C-line occurs substantially on the plus side.

When exceeding an upper limit value of conditional expression (8), the chromatic aberration of magnification of higher-order about the F-line and the g-line occurs substantially on the plus side, and the chromatic aberration of magnification of higher-order about the C-line occurs substantially on the minus side. In such manner, when the chromatic aberration of magnification of higher-order for each wavelength occurs substantially, it becomes a cause of chromatic blurring in a peripheral area of image. At the time of the proximity magnifying observation, since the occurrence of chromatic blurring in the peripheral area of image becomes substantial, the resolving power is degraded in the peripheral area of image. Therefore, exceeding the upper limit value of conditional expression (8) is not preferable.

Furthermore, it is desirable that the following conditional expression (8') is satisfied instead of conditional expression (8):

$$2.5 < f_{G1L4}/f_w < 5.5 \quad (8').$$

By satisfying conditional expression (8'), it is possible to correct more favorably the chromatic aberration of magnification at the time of the proximity magnifying observation.

Moreover, in the objective optical system according to the present embodiment, it is desirable that the following conditional expression (9) is satisfied:

$$-0.65 < f_{G1}/f_{G2} < -0.52 \quad (9),$$

where, $f_{G1}$ denotes a focal length of the first lens group, and $f_{G2}$ denotes a focal length of the second lens group.

Conditional expression (9) is related to a ratio of the focal length of the first lens group and the focal length of the second lens group, and is related to correction of the spherical aberration and the chromatic aberration. By satisfying conditional expression (9), it is possible to correct favorably the spherical aberration and the chromatic aberration.

In a case in which conditional expression (9) is not satisfied, the chromatic aberration of magnification cannot be corrected favorably. As a result, it leads to degradation of image quality, and particularly degradation of image quality in the peripheral area of image.

When falling below a lower limit value of conditional expression (9) and the refractive power of second lens group becomes relatively too large as compared to the refractive power of the first lens group, the chromatic aberration of magnification about the C-line occurs substantially on the minus side, and the chromatic aberration of magnification about the F-line occurs substantially on the plus side. Furthermore, since the spherical aberration occurs substantially on the plus side, this leads to degradation of the resolving power. Therefore, falling below the lower limit value of conditional expression (9) is not preferable.

When exceeding an upper limit value of conditional expression (9), and the refractive power of second lens group becomes relatively too small as compared to the refractive power of the first lens group, conversely, the chromatic aberration of magnification about the C-line occurs substantially on the plus side, and the chromatic aberration of magnification about the F-line occurs substantially on the minus side. Therefore, exceeding the upper limit value of conditional expression (9) is not preferable.

When falling below the lower limit value of conditional expression (9), there is an effect also on the spherical aberration and the longitudinal chromatic aberration. Particularly, since the spherical aberration occurs significantly for a light ray of a low height, an aberration curve is substantially inclined toward the minus side. Moreover, with regard to the longitudinal chromatic aberration, the longitudinal chromatic aberration about the F-line is corrected excessively. Also, correction of coma becomes difficult. Therefore, falling below the lower limit value of conditional expression (9) is not preferable.

Moreover, in the objective optical system according to the present embodiment, it is desirable that the following conditional expression (10) is satisfied:

$$-0.68 < f_{G2}/f_{G3} < -0.49 \quad (10),$$

where, $f_{G2}$ denotes the focal length of the second lens group, and $f_{G3}$ denotes a focal length of the third lens group.

Conditional expression (10) is related to a ratio of the focal length of the second lens group and the focal length of the third lens group. As to whether the refractive power of the second lens group is large or small depends on whether an amount of movement of the second lens group at the time of focusing is large or small. By satisfying conditional expression (10), it is possible to make the optical system small-sized as well as to suppress a fluctuation in aberration at the time of focusing.

When falling below a lower limit value of conditional expression (10), since the refractive power of the second lens group becomes small, the amount of movement of the second lens group at the time of focusing becomes large. Consequently, the optical system becomes large-sized. Moreover, a stroke of driving a lens becomes long. Therefore, in a case of using an actuator in particular as a means for driving the lens, a drive mechanism including the actuator becomes large-sized. Moreover, while moving the lens, since it is necessary to move the lens through a long distance accurately, the drive mechanism is susceptible to become complicated.

When exceeding an upper limit value of conditional expression (10) and the refractive power of the second lens group has become relatively large as compared to the refractive power of the third lens group, error sensitivity at the time of manufacturing becomes large. In the second lens group, a clearance between frames has been provided for the movement. In this case, relative positions of frames fluctuate within the range of clearance. Fluctuation in aberration occurs due to the relative fluctuation of frames, but when the error sensitivity at the time of manufacturing is high, the fluctuation in aberration becomes large. Therefore, exceeding the upper limit value of conditional expression (10) is not preferable.

Furthermore, when exceeding the upper limit value of conditional expression (10), since the focal length of the third lens group becomes large, a back focus of the objective optical system becomes long. Consequently, an overall length of the optical system becomes long, and moreover, an overall length of an image pickup unit including an image pickup element becomes long. In such manner, the objective optical lens and the image pickup unit become large-sized. Therefore, exceeding the upper limit value of conditional expression (10) is not preferable.

Moreover, in the objective optical system according to the present embodiment, it is preferable that the following conditional expression (11) is satisfied:

$$0.2 < EN_w/EN_e < 0.34 \quad (11),$$

where, $EN_w$ denotes a most diagonal entrance-pupil position at the time of focusing to the object point at the long distance, and $EN_e$ denotes a most diagonal entrance-pupil position at the time of focusing to the object point at the close distance.

Conditional expression (11) is related to a position of an entrance pupil at a maximum diagonal, and particularly to a field of view at the time of focusing to the object point at the close distance. Here, $EN_w$ is a distance from a lens surface nearest to the object of the objective optical system up to the most diagonal entrance-pupil position at the time of focusing to the object point at the long distance and $EN_e$ is a distance from the lens surface nearest to object of the objective optical system up to the most diagonal entrance-pupil position at the time of focusing to the object point at the close distance.

When falling below a lower limit value of conditional expression (11), the entrance pupil at the time of focusing to the object point at the close distance is positioned on the object side. Therefore, the field of view at the time of focusing to the object point at the close distance becomes wide. However, since the magnification becomes small by an amount equivalent to an amount by which the field of view has widened, it becomes difficult to secure the magnification necessary for the proximity magnifying observation.

When exceeding an upper limit value of conditional expression (11) and the entrance pupil at the time of focusing to the object point at the close distance is positioned on the image side, the field of view is narrowed excessively. Particularly, at the time of the proximity magnifying observation, a range of only a few µm² to tens of 10 µm² in the field of view can be secured. Therefore, even for slightly improving the observability, it is necessary to secure the field of view of a certain width. Therefore, exceeding the upper limit value of conditional expression (11) is not preferable, and it is desirable to satisfy conditional expression (11).

In the objective optical system according to the present embodiment, it is desirable that the following conditional expression (12) is satisfied:

$$0.28 < EN_w/f_w < 0.43 \qquad (12),$$

where, $EN_w$ denotes the most diagonal entrance-pupil position at the time of focusing to the object point at the long distance, and $f_w$ denotes the focal length of the overall objective optical system at the time of focusing to the object point at the long distance.

Conditional expression (12) is related to the position of the entrance pupil at a maximum diagonal, and to an outer diameter of the lens system.

When falling below a lower limit value of conditional expression (12), the entrance pupil at the maximum diagonal, at the time of focusing to the object point at the long distance, is positioned on the image side. Consequently, it is possible to make small a diameter of the lens positioned nearest to the object. However, since this leads to an increase in a diameter of the lens positioned nearest to the image, the optical system becomes large-sized. Therefore, falling below the lower limit value of conditional expression (12) is not preferable.

When exceeding an upper limit value of conditional expression (12), the entrance pupil at the maximum diagonal, at the time of focusing to the object point at the long distance, is positioned on the object side. Consequently, the diameter of the lens positioned on the object side becomes large.

Moreover, in the objective optical system according to the present embodiment, it is preferable that the following conditional expression (13) is satisfied:

$$-6 < R_{3GLi}/f_e < -1.7 \qquad (13),$$

where, $R_{3GLi}$ denotes a radius of curvature on the object side of a lens positioned nearest to an image in the third lens group, and $f_e$ denotes the focal length of the objective optical system at the time of focusing to the object point at the close distance.

Conditional expression (13) is related to the lens positioned nearest to the image in the third lens group. Conditional expression (13) is related to the correction of the longitudinal chromatic aberration and the curvature of field.

When falling below a lower limit value of conditional expression (13), the refractive power of a negative lens positioned nearest to the image becomes large. Consequently, in the normal observation and the proximity magnifying observation, a fluctuation in an image plane, for example, a fluctuation in a position of the image plane and a fluctuation in an inclination of the image plane become large. Therefore, falling below the lower limit value of conditional expression (13) is not preferable.

When exceeding an upper limit value of conditional expression (13), the refractive power of the negative lens positioned nearest to the image becomes small. In this case, the capacity of correcting chromatic aberration is reduced. Consequently, deterioration of the longitudinal chromatic aberration becomes remarkable. In other words, at the time of the normal observation, the longitudinal chromatic aberration about the C-line occurs substantially on the minus side and the longitudinal chromatic aberration about the F-line occurs substantially on the plus side. Whereas, at the time of the proximity magnifying observation, the longitudinal chromatic aberration about the C-line occurs substantially on the plus side, and the longitudinal chromatic aberration about the F-line occurs substantially on the minus side. In both the observations, the resolving power at an image center is degraded. Therefore, exceeding the upper limit value of conditional expression (13) is not preferable.

Moreover, in the objective optical system according to the present embodiment, it is desirable that the following conditional expression (14) is satisfied.

$$-1.7 < f_{G2}/f_w < -1.3 \qquad (14)$$

where, $f_{G2}$ denotes the focal length of the second lens group, and
$f_w$ denotes the focal length of the overall objective optical system at the time of focusing to the object point at the long distance.

When falling below a lower limit value of conditional expression (14), in all observation states from the normal observation to the proximity magnifying observation, the image plane is inclined toward the plus side. Therefore, falling below the lower limit value of conditional expression (14) is not preferable.

When an upper limit value of conditional expression (14) is exceeded, in all observation states from the normal observation to the proximity magnifying observation, correction of the spherical aberration is excessive. Therefore, exceeding the upper limit value of conditional expression (14) is not preferable.

Moreover, in the objective optical system according to the present embodiment, it is desirable that the following conditional expression (15) is satisfied:

$$0.1 < \Delta_{2G}/LTL < 0.17 \qquad (15),$$

where, $\Delta_{2G}$ denotes an amount of movement of the second lens group when focused from the object point at the long distance to the object point at the close distance, and LTL denotes a overall length of the objective optical system.

When falling below the lower limit value of conditional expression (15) and the amount of movement of the second lens group becomes small, a focusing sensitivity becomes excessively high. Therefore, falling below the lower limit value of conditional expression (15) is not preferable. Particularly, in a case in which the object point is at a position of a state close to the proximity magnifying observation, when the second lens group is moved even slightly, an imaging surface moves immediately. Thus, when falling below the lower limit value of conditional expression (15), the objective optical system becomes an optical system in which focusing becomes difficult.

When exceeding an upper limit value of conditional expression (15), the amount of movement of the second lens group becomes excessively large. The overall length of the optical system becomes long due to the excessively large amount of movement of the second lens group. Therefore, exceeding the upper limit value of conditional expression (15) is not preferable.

Moreover, in the objective optical system according to the present embodiment, it is desirable that a diameter of the aperture stop is constant when the aperture stop moves along the optical axis.

In an aperture stop in which an aperture diameter changes, a mechanism which changes the aperture diameter is necessary. Since a driving means (such as an actuator) for driving the second lens has already been disposed in the insertion portion, installing such mechanism leads to further increase in diameter of a lens frame which accommodates the objective optical system. Therefore, it is not preferable to use an aperture stop of which the aperture diameter changes.

Moreover, the objective optical system according to the present embodiment can also be used in an optical instrument other than endoscope.

For instance, in an image pickup optical system of a digital camera, it is possible to use the objective optical system according to the present embodiment. In photography by a digital camera, sometimes macro photography beyond equal magnification is carried out. In such case, as an amount of drawing out of lens becomes large, a macro-converter lens is used in many cases. However, by using the objective optical system according to the present embodiment as an image pickup optical system, without installing the macro-converter lens, it is possible to carry out macro photography with a higher magnification than ever before.

Moreover, generally, in a macro lens, the first lens group is drawn out toward the object side, and focusing is carried out by floating of a plurality of lens groups. However, when the objective optical system according to the present embodiment is used, macro photography with inner focusing is possible. Therefore, it is advantageous in a case of photographing after determining a working distance.

Furthermore, the objective optical system according to the present embodiment can also be used for an image pickup optical system of portable equipment such as a camera of a mobile telephone. By doing so, the macro photography is readily enjoyable.

Example 1

Figure 2A:
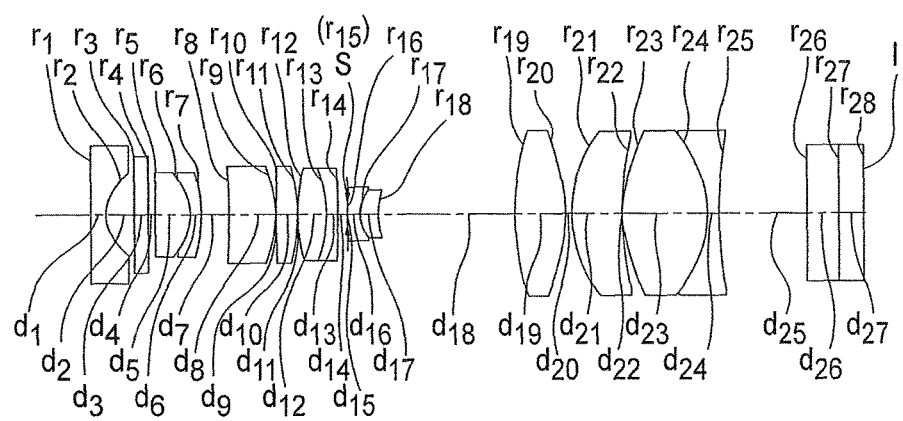
FIG. 2A, FIG. 2B, and FIG. 2C are diagrams showing a cross-sectional arrangement of an objective optical system according to an example 1 of the present invention, where.
Figure 2B:
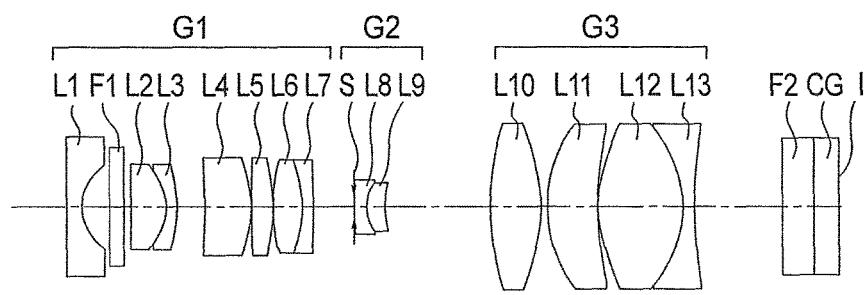
Figure 2C:
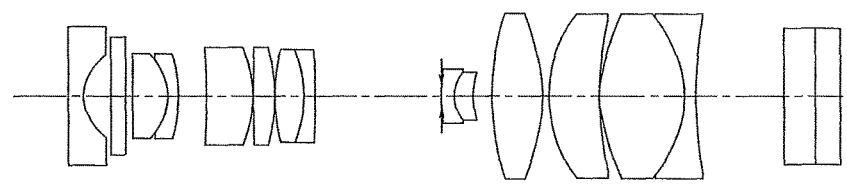

An objective optical system according to an example 1 will be described below. FIG. 2A, FIG. 2B, and FIG. 2C are lens cross-sectional views of the objective optical system according to the example 1, where, FIG. 2A is a cross-sectional view in a normal observation state, FIG. 2B is a cross-sectional view in an intermediate state, and FIG. 2C is a cross-sectional view in a proximity magnifying observation state.

The objective optical system of the example 1, as shown in FIG. 2A, FIG. 2B, and FIG. 2C, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a negative meniscus lens L3 having a convex surface directed toward the image side, a positive meniscus lens L4 having a convex surface directed toward the image side, a positive meniscus lens L5 having a convex surface directed toward the image side, a biconvex positive lens L6, and a negative meniscus lens L7 having a convex surface directed toward the image side. Here, the positive meniscus lens L2 and the negative meniscus lens L3 form a cemented lens having a negative refractive power. The biconvex positive lens L6 and the negative meniscus lens L7 form a cemented lens having a positive refractive power.

The second lens group G2 includes a biconcave negative lens L8 and a positive meniscus lens L9 having a convex surface directed toward the object side. Here, the biconcave negative lens L8 and the positive meniscus lens L9 form a cemented lens having a negative refractive power.

An aperture stop S is disposed between the first lens group G1 and the second lens group G2. More elaborately, the aperture stop S is disposed nearest to an object in the second lens group G2.

The third lens group G3 includes a biconvex positive lens L10, a positive meniscus lens L11 having a convex surface directed toward the object side, a planoconvex positive lens L12, and a planoconcave negative lens L13. Here, the biconvex positive lens L12 and the planoconcave negative lens L13 form a cemented lens having a negative refractive power.

A plane-parallel plate F1 is disposed on the image side of the planoconcave negative lens L1. A plane-parallel plate F2 and a cover glass CG are disposed on the image side of the third lens group G3.

At the time of focusing, the second lens group G2 and the aperture stop S move integrally. When focusing is carried out from a state of being focused to an object point at a long distance to an object point at a close distance, the second lens group G2 and the aperture stop S move toward the image side.

The objective optical system of the example 1 has the abovementioned basic arrangement, and satisfies each of conditional expressions (1) to (15). Moreover, by letting a focal length of each lens group from the first lens group G1 to the third lens group G3 to be an appropriate value, there is no degradation of image quality, and a compact objective optical system is realized.

FIG. 3A, FIG. 3B, FIG. 3C, and FIG. 3D are aberration diagrams of a spherical aberration (SA), an astigmatism (AS), a distortion (DT), and a chromatic aberration of magnification (CC) respectively in the normal observation state of the example 1, FIG. 3E, FIG. 3F, FIG. 3G, and FIG. 3H are aberration diagrams of a spherical aberration (SA), an astigmatism (AS), a distortion (DT), and a chromatic aberration of magnification (CC) respectively in the intermediate state of the example 1, and FIG. 3I, FIG. 3J, FIG. 3K, and FIG. 3L are aberration diagrams of a spherical aberration (SA), an astigmatism (AS), a distortion (DT), and a chromatic aberration of magnification (CC) respectively in the proximity magnifying observation state of the example 1.

In each aberration diagram, a longitudinal axis indicates an aberration amount. The unit of aberration amount for the spherical aberration, the astigmatism, and the chromatic aberration of magnification is mm. Moreover, the unit of aberration amount for the distortion is %. Furthermore, ω is a half angle of view, and the unit of ω is ° (degrees), and Fno denotes an F-number. The unit of a wavelength of an aberration curve is nm. These symbols are same in other examples as well.

Example 2

Figure 4A:
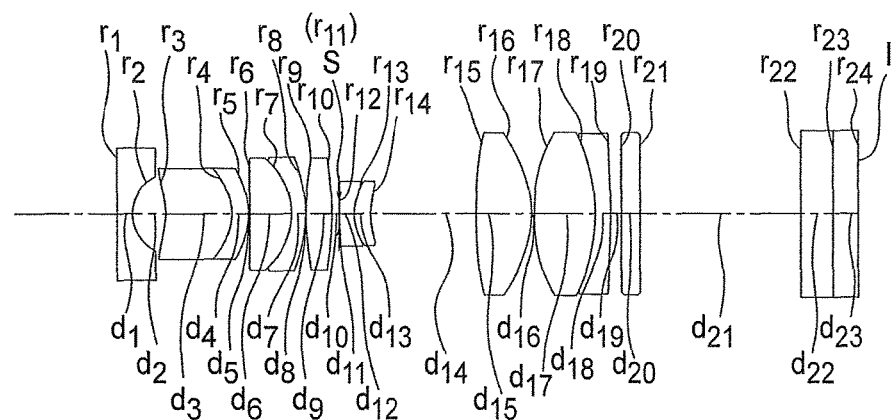
FIG. 4A, FIG. 4B, and FIG. 4C are diagrams showing a cross-sectional arrangement of an objective optical system according to an example 2 of the present invention, where.
Figure 4B:
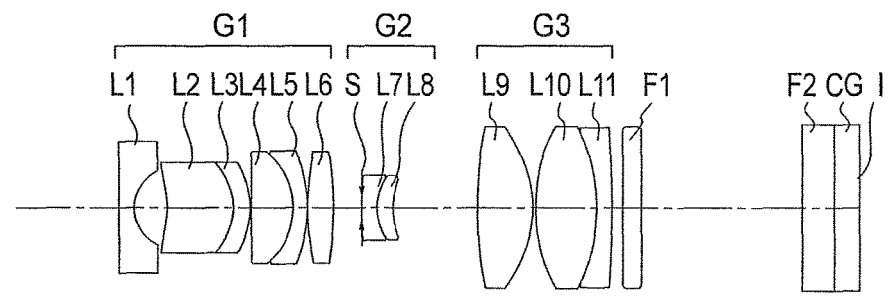
Figure 4C:
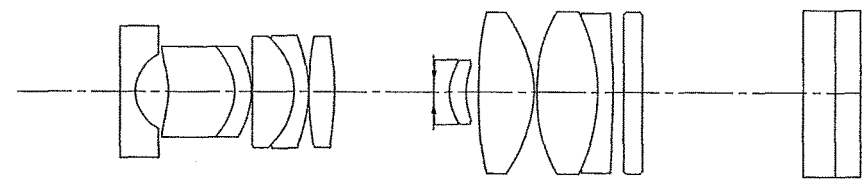

An objective optical system according to an example 2 will be described below. FIG. 4A, FIG. 4B, and FIG. 4C are lens cross-sectional views of the objective optical system according to the example 2, where, FIG. 4A is a cross-sectional view in a normal observation state, FIG. 4B is a cross-sectional view in an intermediate state, and FIG. 4C is a cross-sectional view in a proximity magnifying observation state.

The objective optical system of the example 2, as shown in FIG. 4A, FIG. 4B, and FIG. 4C, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a negative meniscus lens L3 having a convex surface directed toward the image side, a planoconvex positive lens L4 having a convex surface directed toward the image side, a negative meniscus lens L5 having a convex surface directed toward the image side, and a biconvex positive lens L6. Here, the positive meniscus lens L2 and the negative meniscus lens L3 form a cemented lens having a positive refractive power. The planoconvex positive lens L4 and the negative meniscus lens L5 form a cemented lens having a positive refractive power.

The second lens group G2 includes a biconcave negative lens L7 and a positive meniscus lens L8 having a convex surface directed toward the object side. Here, the biconcave negative lens L7 and the positive meniscus lens L8 form a cemented lens having a negative refractive power.

An aperture stop S is disposed between the first lens group G1 and the second lens group G2. More elaborately, the aperture stop S is disposed nearest to an object in the second lens group G2.

The third lens group G3 includes a biconvex positive lens L9, a biconvex positive lens L10, and a negative meniscus lens L11 having a convex surface directed toward the image side. Here, the biconvex positive lens L10 and the negative meniscus lens L11 form a cemented lens having a positive refractive power.

A plane-parallel plate F1, a plane-parallel plate F2, and a cover glass CG are disposed on the image side of the third lens group G3.

At the time of focusing, the second lens group G2 and the aperture stop S move integrally. When focusing is carried out from a state of being focused to an object point at a long distance to an object point at a close distance, the second lens group G2 and the aperture stop S move toward the image side.

The objective optical system of the example 2 has the abovementioned basic arrangement, and satisfies each of conditional expressions (1) to (15). Moreover, by letting a focal length of each lens group from the first lens group G1 to the third lens group G3 to be an appropriate value, there is no degradation of image quality, and a compact objective optical system is realized.

FIG. 5A, FIG. 5B, FIG. 5C, and FIG. 5D are aberration diagrams of a spherical aberration (SA), an astigmatism (AS), a distortion (DT), and a chromatic aberration of magnification (CC) respectively in the normal observation state of the example 2, FIG. 5E, FIG. 5F, FIG. 5G, and FIG. 5H are aberration diagrams of a spherical aberration (SA), an astigmatism (AS), a distortion (DT), and a chromatic aberration of magnification (CC) respectively in the intermediate state of the example 2, and FIG. 5I, FIG. 5J, FIG. 5K, and FIG. 5L are aberration diagrams of a spherical aberration (SA), an astigmatism (AS), a distortion (DT), and a chromatic aberration of magnification (CC) respectively in the proximity magnifying observation state of the example 2.

Example 3

Figure 6A:
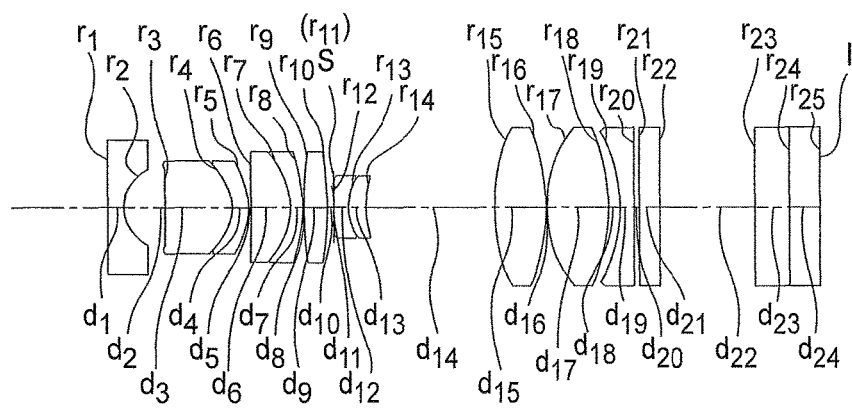
FIG. 6A, FIG. 6B, and FIG. 6C are diagrams showing a cross-sectional arrangement of an objective optical system according to an example 3 of the present invention, where.
Figure 6B:
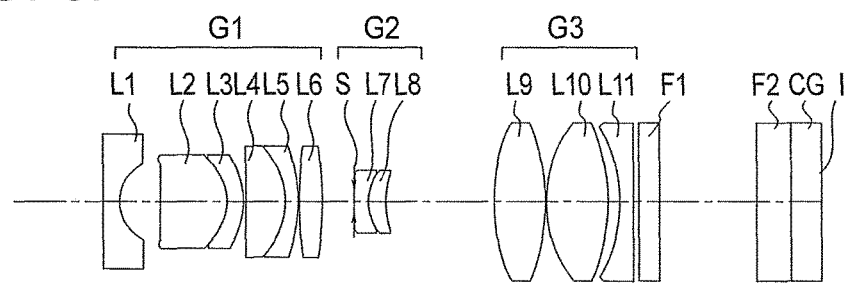
Figure 6C:
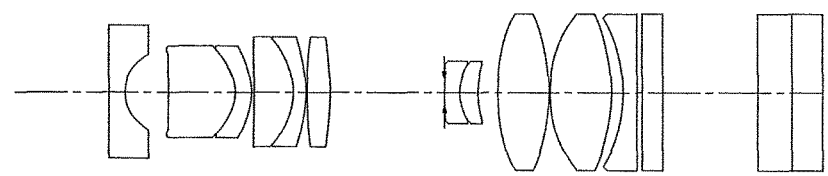

An objective optical system according to an example 3 will be described below. FIG. 6A, FIG. 6B, and FIG. 6C are lens cross-sectional views of the objective optical system according to the example 3, where, FIG. 6A is a cross-sectional view in a normal observation state, FIG. 6B is a cross-sectional view in an intermediate state, and FIG. 6C is a cross-sectional view in a proximity magnifying observation state.

The objective optical system of the example 3, as shown in FIG. 6A, FIG. 6B, and FIG. 6C, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a negative meniscus lens L3 having a convex surface directed toward the image side, a planoconvex positive lens L4 having a convex surface directed toward the image side, a negative meniscus lens L5 having a convex surface directed toward the image side, and a biconvex positive lens L6. Here, the positive meniscus lens L2 and the negative meniscus lens L3 form a cemented lens having a positive refractive power. The planoconvex positive lens L4 and the negative meniscus lens L5 form a cemented lens having a positive refractive power.

The second lens group G2 includes a biconcave negative lens L7 and a positive meniscus lens L8 having a convex surface directed toward the object side. Here, the biconcave negative lens L7 and the positive meniscus lens L8 form a cemented lens having a negative refractive power.

An aperture stop S is disposed between the first lens group G1 and the second lens group G2. More elaborately, the aperture stop S is disposed nearest to an object in the second lens group G2.

The third lens group G3 includes a biconvex positive lens L9, a biconvex positive lens L10, and a planoconcave negative lens L11 of which an image side is a flat surface.

A plane-parallel plate F1, a plane-parallel plate F2, and a cover glass CG are disposed on the image side of the third lens group G3.

At the time of focusing, the second lens group G2 and the aperture stop S move integrally. When focusing is carried out from a state of being focused to an object point at a long distance to an object point at a close distance, the second lens group G2 and the aperture stop S move toward the image side.

The objective optical system of the example 3 has the abovementioned basic arrangement, and satisfies each of conditional expressions (1) to (15). Moreover, by letting a focal length of each lens group from the first lens group G1 to the third lens group G3 to be an appropriate value, there is no degradation of image quality, and a compact objective optical system is realized.

FIG. 7A, FIG. 7B, FIG. 7C, and FIG. 7D are aberration diagrams of a spherical aberration (SA), an astigmatism (AS), a distortion (DT), and a chromatic aberration of magnification (CC) respectively in the normal observation state of the example 3, FIG. 7E, FIG. 7F, FIG. 7G, and FIG. 7H are aberration diagrams of a spherical aberration (SA), an astigmatism (AS), a distortion (DT), and a chromatic aberration of magnification (CC) respectively in the intermediate state of the example 3, and FIG. 7I, FIG. 7J, FIG. 7K, and FIG. 7L are aberration diagrams of a spherical aberration (SA), an astigmatism (AS), a distortion (DT), and a chromatic aberration of magnification (CC) respectively in the proximity magnifying observation state of the example 3.

Example 4

Figure 8A:
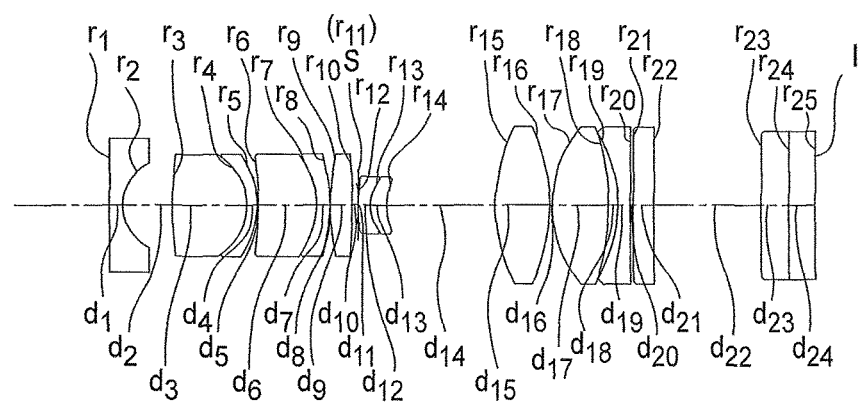
FIG. 8A, FIG. 8B, and FIG. 8C are diagrams showing a cross-sectional arrangement of an objective optical system according to an example 4 of the present invention, where.
Figure 8B:
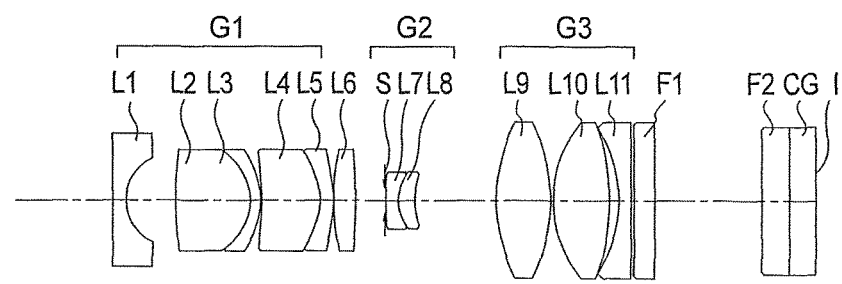
Figure 8C:
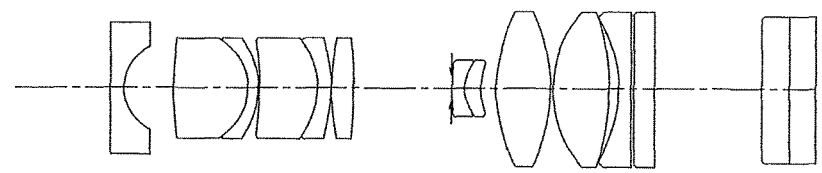

An objective optical system according to an example 4 will be described below. FIG. 8A, FIG. 8B, and FIG. 8C are lens cross-sectional views of the objective optical system according to the example 4, where, FIG. 8A is a cross-sectional view in a normal observation state, FIG. 8B is a cross-sectional view in an intermediate state, and FIG. 8C is a cross-sectional view in a proximity magnifying observation state.

The objective optical system of the example 4, as shown in FIG. 8A, FIG. 8B, and FIG. 8C, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a biconvex positive lens L2, a negative meniscus lens L3 having a convex surface directed toward an image side, a positive meniscus lens L4 having a convex surface directed toward the image side, a negative meniscus lens L5 having a convex surface directed toward the image side, and a biconvex positive lens L6. Here, the biconvex positive lens L2 and the negative meniscus lens L3 form a cemented lens having a positive refractive power. The positive meniscus lens L4 and the negative meniscus lens L5 form a cemented lens having a positive refractive power.

The second lens group G2 includes a biconcave negative lens L7 and a positive meniscus lens L8 having a convex surface directed toward the object side. Here, the biconcave negative lens L7 and the positive meniscus lens L8 form a cemented lens having a negative refractive power.

An aperture stop S is disposed between the first lens group G1 and the second lens group G2. More elaborately, the aperture stop S is disposed nearest to an object in the second lens group G2.

The third lens group G3 includes a biconvex positive lens L9, a biconvex positive lens L10, and a planoconcave negative lens L11 of which an image side is a flat surface.

A plane-parallel plate F1, a plane-parallel plate F2, and a cover glass CG are disposed on the image side of the third lens group G3.

At the time of focusing, the second lens group G2 and the aperture stop S move integrally. When focusing is carried out from a state of being focused to an object point at a long distance to an object point at a close distance, the second lens group G2 and the aperture stop S move toward the image side.

The objective optical system of the example 4 has the abovementioned basic arrangement, and satisfies each of conditional expressions (1) to (15). Moreover, by letting a focal length of each lens group from the first lens group G1 to the third lens group G3 to be an appropriate value, there is no degradation of image quality, and a compact objective optical system is realized.

FIG. 9A, FIG. 9B, FIG. 9C, and FIG. 9D are aberration diagrams of a spherical aberration (SA), an astigmatism (AS), a distortion (DT), and a chromatic aberration of magnification (CC) respectively in the normal observation state of the example 4, FIG. 9E, FIG. 9F, FIG. 9G, and FIG. 9H are aberration diagrams of a spherical aberration (SA), an astigmatism (AS), a distortion (DT), and a chromatic aberration of magnification (CC) respectively in the intermediate state of the example 4, and FIG. 9I, FIG. 9J, FIG. 9K, and FIG. 9L are aberration diagrams of a spherical aberration (SA), an astigmatism (AS), a distortion (DT), and a chromatic aberration of magnification (CC) respectively in the proximity magnifying observation state of the example 4.

Example 5

Figure 10A:
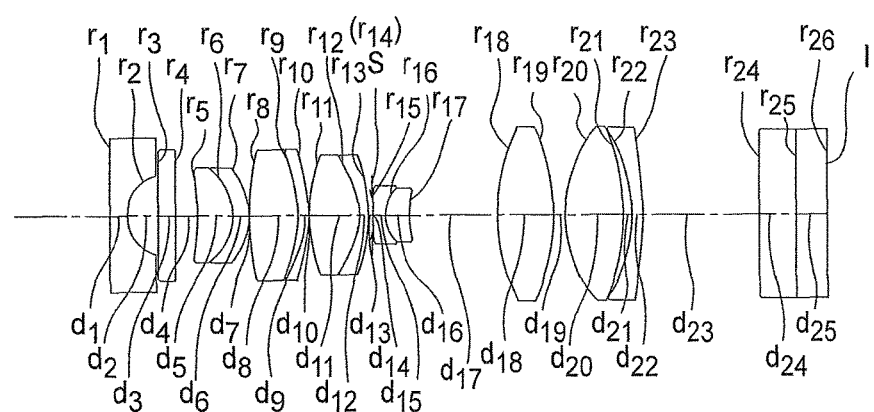
FIG. 10A, FIG. 10B, and FIG. 10C are diagrams showing a cross-sectional arrangement of an objective optical system according to an example 5 of the present invention, where.
Figure 10B:
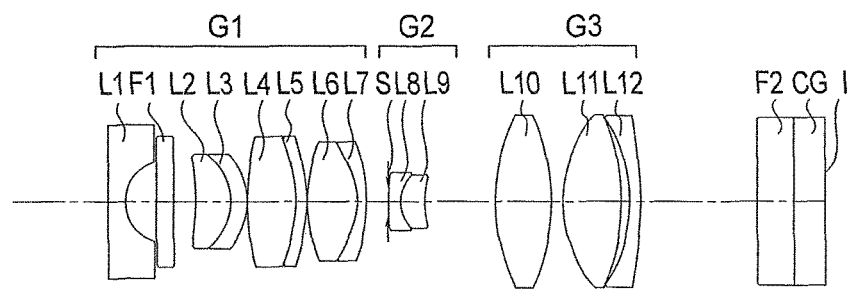
Figure 10C:
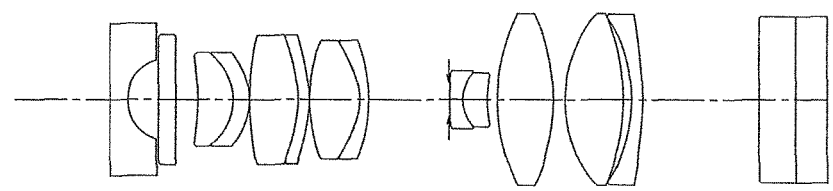

An objective optical system according to an example 5 will be described below. FIG. 10A, FIG. 10B, and FIG. 10C are lens cross-sectional views of the objective optical system according to the example 5, where, FIG. 10A is a cross-sectional view in a normal observation state, FIG. 10B is a cross-sectional view in an intermediate state, and FIG. 10C is a cross-sectional view in a proximity magnifying observation state.

The objective optical system of the example 5, as shown in FIG. 10A, FIG. 10B, and FIG. 10C, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a negative meniscus lens L3 having a convex surface directed toward the image side, a biconvex positive lens L4, a negative meniscus lens L5 having a convex surface directed toward the image side, a biconvex positive lens L6, and a negative meniscus lens L7 having a convex surface directed toward the image side. Here, the positive meniscus lens L2 and the negative meniscus lens L3 form a cemented lens having a positive refractive power. The biconvex positive lens L4 and the negative meniscus lens L5 form a cemented lens having a positive refractive power. The biconvex positive lens L6 and the negative meniscus lens L7 form a cemented lens having a positive refractive power.

The second lens group G2 includes a biconcave negative lens L8 and a positive meniscus lens L9 having a convex surface directed toward the object side. Here, the biconcave negative lens L8 and the positive meniscus lens L9 form a cemented lens having a negative refractive power.

An aperture stop S is disposed between the first lens group G1 and the second lens group G2. More elaborately, the aperture stop S is disposed nearest to an object in the second lens group G2.

The third lens group G3 includes a biconvex positive lens L10, a biconvex positive lens L11, and a negative meniscus lens L12 having a convex surface directed toward the image side.

A plane-parallel plate F1 is disposed on the image side of the planoconcave negative lens L1. A plane-parallel plate F2 and a cover glass CG are disposed on the image side of the third lens group G3.

At the time of focusing, the second lens group G2 and the aperture stop S move integrally. When focusing is carried out from a state of being focused to an object point at a long distance to an object point at a close distance, the second lens group G2 and the aperture stop S move toward the image side.

The objective optical system of the example 5 has the abovementioned basic arrangement, and satisfies each of conditional expressions (1) to (15). Moreover, by letting a focal length of each lens group from the first lens group G1 to the third lens group G3 to be an appropriate value, there is no degradation of image quality, and a compact objective optical system is realized.

FIG. 11A, FIG. 11B, FIG. 11C, and FIG. 11D are aberration diagrams of a spherical aberration (SA), an astigmatism (AS), a distortion (DT), and a chromatic aberration of magnification (CC) respectively in the normal observation state of the example 5, FIG. 11E, FIG. 11F, FIG. 11G, and FIG. 11H are aberration diagrams of a spherical aberration (SA), an astigmatism (AS), a distortion (DT), and a chromatic aberration of magnification (CC) respectively in the intermediate state of the example 5, and FIG. 11I, FIG. 11J, FIG. 11K, and FIG. 11L are aberration diagrams of a spherical aberration (SA), an astigmatism (AS), a distortion (DT), and a chromatic aberration of magnification (CC) respectively in the proximity magnifying observation state of the example 5.

Example 6

Figure 12A:
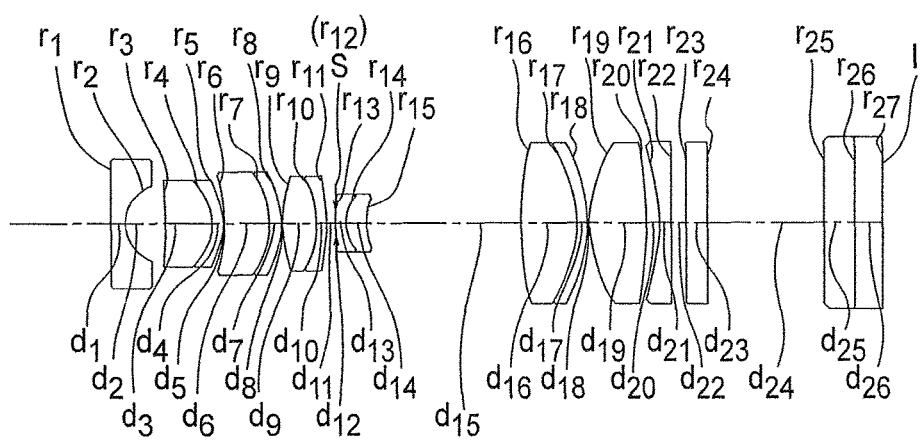
FIG. 12A, FIG. 12B, and FIG. 12C are diagrams showing a cross-sectional arrangement of an objective optical system according to an example 6 of the present invention, where.
Figure 12B:
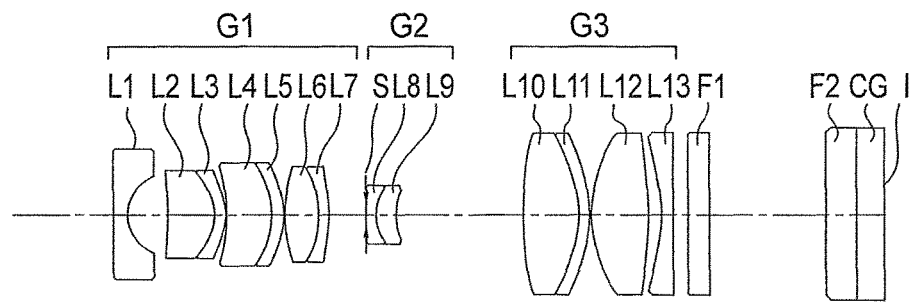
Figure 12C:
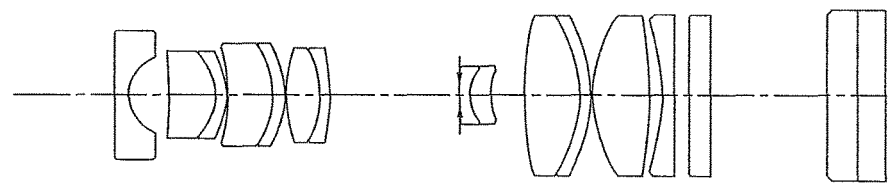

An objective optical system according to an example 6 will be described below. FIG. 12A, FIG. 12B, and FIG. 12C are lens cross-sectional views of the objective optical system according to the example 6, where, FIG. 12A is a cross-sectional view in a normal observation state, FIG. 12B is a cross-sectional view in an intermediate state, and FIG. 12C is a cross-sectional view in a proximity magnifying observation state.

The objective optical system of the example 6, as shown in FIG. 12A, FIG. 12B, and FIG. 12C, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a negative meniscus lens L3 having a convex surface directed toward the image side, a positive meniscus lens L4 having a convex surface directed toward the image side, a negative meniscus lens L5 having a convex surface directed toward the image side, a biconvex positive lens L6, and a negative meniscus lens L7 having a convex surface directed toward the image side. Here, the positive meniscus lens L2 and the negative meniscus lens L3 form a cemented lens having a positive refractive power. The positive meniscus lens L4 and the negative meniscus lens L5 form a cemented lens having a positive refractive power. The biconvex positive lens L6 and the negative meniscus lens L7 form a cemented lens having a positive refractive power.

The second lens group G2 includes a biconcave negative lens L8 and a positive meniscus lens L9 having a convex surface directed toward the object side. Here, the biconcave negative lens L8 and the positive meniscus lens L9 form a cemented lens having a negative refractive power.

An aperture stop S is disposed between the first lens group G1 and the second lens group G2. More elaborately, the aperture stop S is disposed nearest to an object in the second lens group G2.

The third lens group G3 includes a biconvex positive lens L10, a negative meniscus lens L11 having a convex surface directed toward the image side, a biconvex positive lens L12, and a planoconcave negative lens L13 of which an image side is a flat surface. Here, the biconvex positive lens L10 and the negative meniscus lens L11 form a cemented lens having a positive refractive power.

A plane-parallel plate F1, a plane-parallel plate F2, and a cover glass CG are disposed on the image side of the third lens group G3.

At the time of focusing, the second lens group G2 and the aperture stop S move integrally. When focusing is carried out from a state of being focused to an object point at a long distance to an object point at a close distance, the second lens group G2 and the aperture stop S move toward the image side.

The objective optical system of the example 6 has the abovementioned basic arrangement, and satisfies each of conditional expressions (1) to (15). Moreover, by letting a focal length of each lens group from the first lens group G1 to the third lens group G3 to be an appropriate value, there is no degradation of image quality, and a compact objective optical system is realized.

FIG. 13A, FIG. 13B, FIG. 13C, and FIG. 13D are aberration diagrams of a spherical aberration (SA), an astigmatism (AS), a distortion (DT), and a chromatic aberration of magnification (CC) respectively in the normal observation state of the example 6, FIG. 13E, FIG. 13F, FIG. 13G, and FIG. 13H are aberration diagrams of a spherical aberration (SA), an astigmatism (AS), a distortion (DT), and a chromatic aberration of magnification (CC) respectively in the intermediate state of the example 6, and FIG. 13I, FIG. 13J, FIG. 13K, and FIG. 13L are aberration diagrams of a spherical aberration (SA), an astigmatism (AS), a distortion (DT), and a chromatic aberration of magnification (CC) respectively in the proximity magnifying observation state of the example 6.

Example 7

Figure 14A:
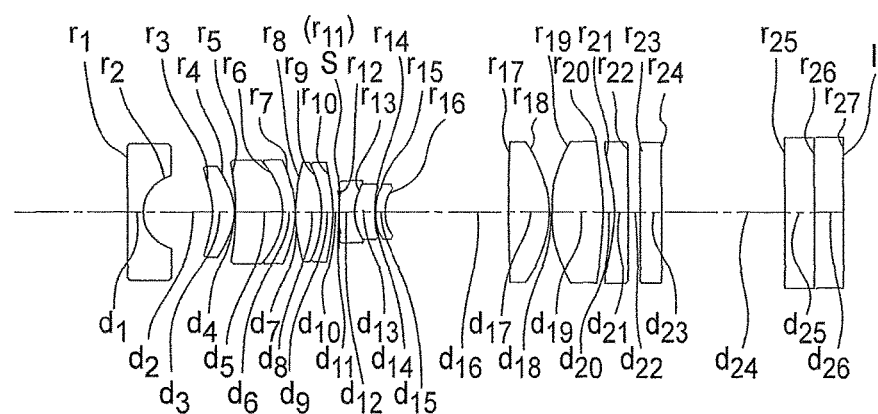
FIG. 14A, FIG. 14B, and FIG. 14C are diagrams showing a cross-sectional arrangement of an objective optical system according to an example 7 of the present invention, where.
Figure 14B:
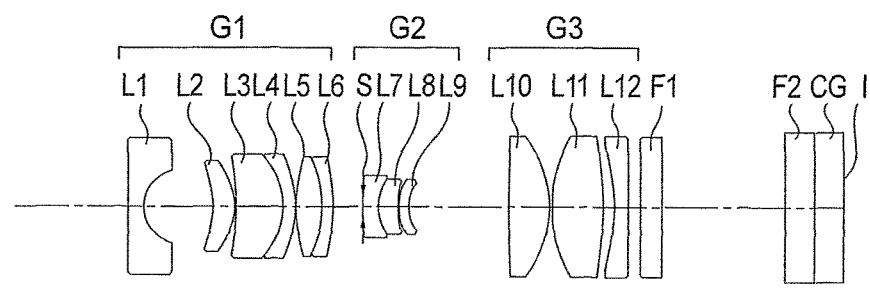
Figure 14C:
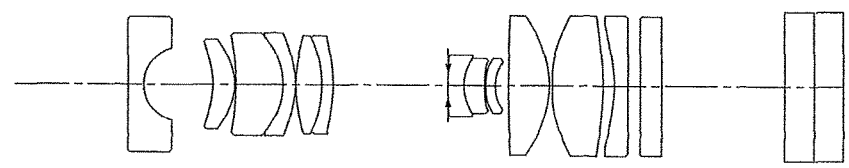
Figures 15A, 15B, 15C, 15D:
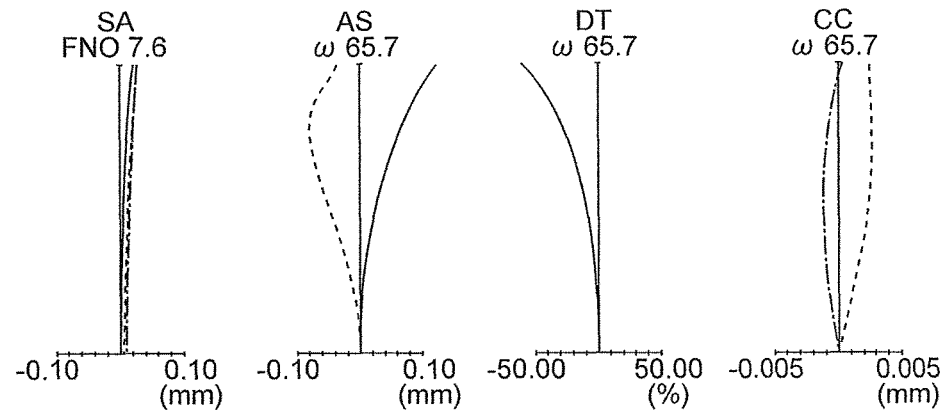
FIG. 15A, FIG. 15B, FIG. 15C, FIG. 15D, FIG. 15E, FIG. 15F, FIG. 15G, FIG. 15H, FIG. 15I, FIG. 15J, FIG. 15K, and FIG. 15L are aberration diagrams showing a spherical aberration (SA), an astigmatism (AS), a distortion (DT), and a chromatic aberration of magnification (CC) of the example 7.
Figures 15E, 15F, 15G, 15H:
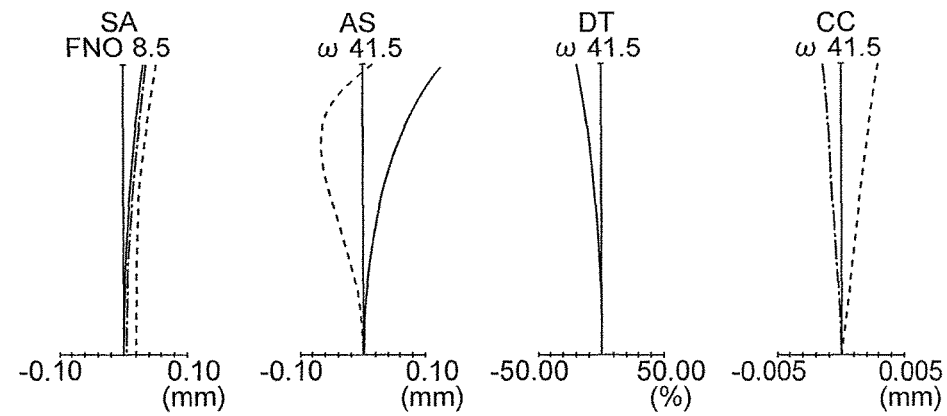
Figures 15I, 15J, 15K, 15L:
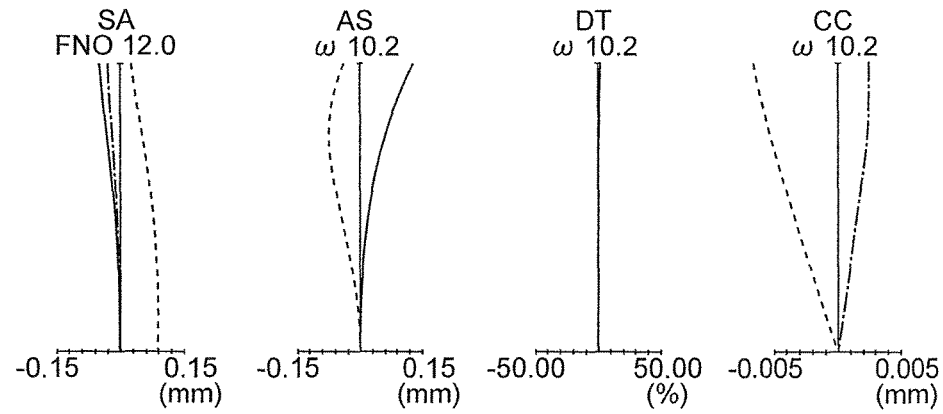

An objective optical system according to an example 7 will be described below. FIG. 14A, FIG. 14B, and FIG. 14C are lens cross-sectional views of the objective optical system according to the example 7, where, FIG. 14A is a cross-sectional view in a normal observation state, FIG. 14B is a cross-sectional view in an intermediate state, and FIG. 14C is a cross-sectional view in a proximity magnifying observation state.

The objective optical system of the example 7, as shown in FIG. 14A, FIG. 14B, and FIG. 14C, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a positive meniscus lens L3 having a convex surface directed toward the image side, a negative meniscus lens L4 having a convex surface directed toward the image side, a biconvex positive lens L5, and a negative meniscus lens L6 having a convex surface directed toward the image side. Here, the positive meniscus lens L3 and the negative meniscus lens L4 form a cemented lens having a positive refractive power. The biconvex positive lens L5 and the negative meniscus lens L6 form a cemented lens having a positive refractive power.

The second lens group G2 includes a biconcave negative lens L7, a positive meniscus lens L8 having a convex surface directed toward the object side, and a negative meniscus lens L9 having a convex surface directed toward the object side. Here, the biconcave negative lens L7 and the positive meniscus lens L8 form a cemented lens having a negative refractive power.

An aperture stop S is disposed between the first lens group G1 and the second lens group G2. More elaborately, the aperture stop S is disposed nearest to an object in the second lens group G2.

The third lens group G3 includes a biconvex positive lens L10, a biconvex positive lens L11, and a planoconcave negative lens L12 of which an image side is a flat surface.

A plane-parallel plate F1, a plane-parallel plate F2, and a cover glass CG are disposed on the image side of the third lens group G3.

At the time of focusing, the second lens group G2 and the aperture stop S move integrally. When focusing is carried out from a state of being focused to an object point at a long distance to an object point at a close distance, the second lens group G2 and the aperture stop S move toward the image side.

The objective optical system of the example 7 has the abovementioned basic arrangement, and satisfies each of conditional expressions (1) to (15). Moreover, by letting a focal length of each lens group from the first lens group G1 to the third lens group G3 to be an appropriate value, there is no degradation of image quality, and a compact objective optical system is realized.

FIG. 15A, FIG. 15B, FIG. 15C, and FIG. 15D are aberration diagrams of a spherical aberration (SA), an astigmatism (AS), a distortion (DT), and a chromatic aberration of magnification (CC) respectively in the normal observation state of the example 7, FIG. 15E, FIG. 15F, FIG. 15G, and FIG. 15H are aberration diagrams of a spherical aberration (SA), an astigmatism (AS), a distortion (DT), and a chromatic aberration of magnification (CC) respectively in the intermediate state of the example 7, and FIG. 15I, FIG. 15J, FIG. 15K, and FIG. 15L are aberration diagrams of a spherical aberration (SA), an astigmatism (AS), a distortion (DT), and a chromatic aberration of magnification (CC) respectively in the proximity magnifying observation state of the example 7.

Example 8

Figure 16A:
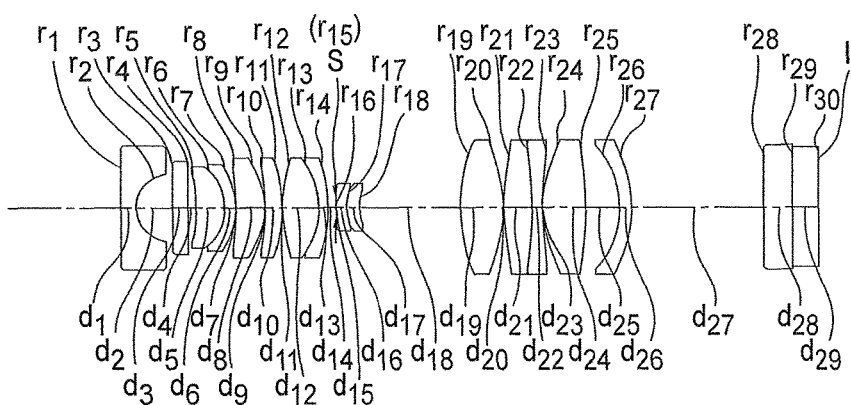
FIG. 16A, FIG. 16B, and FIG. 16C are diagrams showing a cross-sectional arrangement of an objective optical system according to an example 8 of the present invention, where.
Figure 16B:
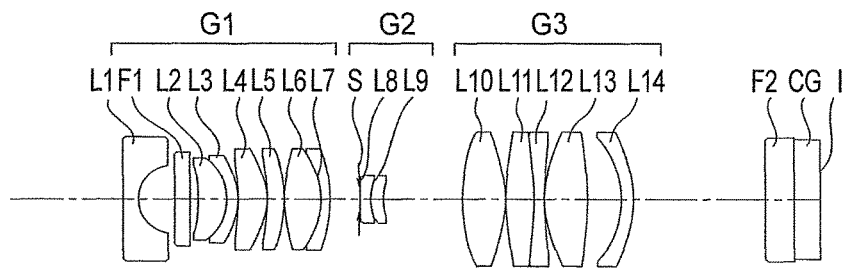
Figure 16C:
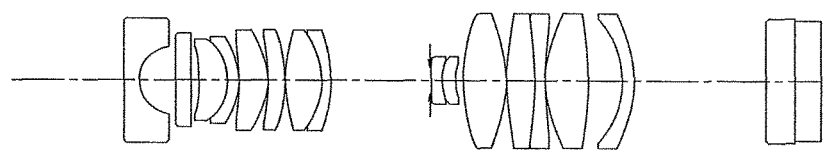
Figures 17A, 17B, 17C, 17D:
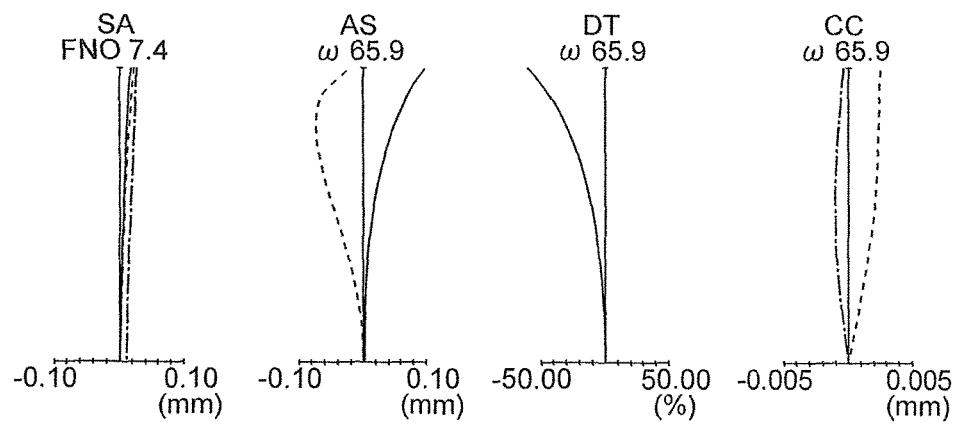
FIG. 17A, FIG. 17B, FIG. 17C, FIG. 17D, FIG. 17E, FIG. 17F, FIG. 17G, FIG. 17H, FIG. 17I, FIG. 17J, FIG. 17K, and FIG. 17L are aberration diagrams showing a spherical aberration (SA), an astigmatism (AS), a distortion (DT), and a chromatic aberration of magnification (CC) of the example 8.
Figures 17E, 17F, 17G, 17H:
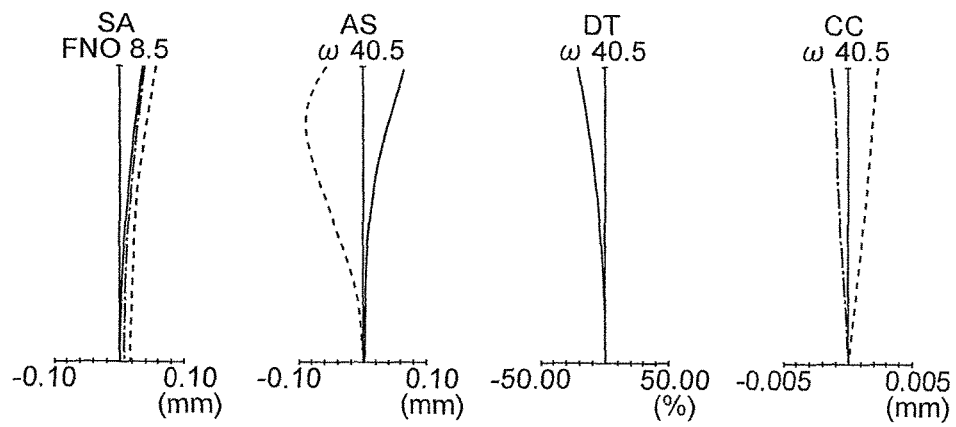
Figures 17I, 17J, 17K, 17L:
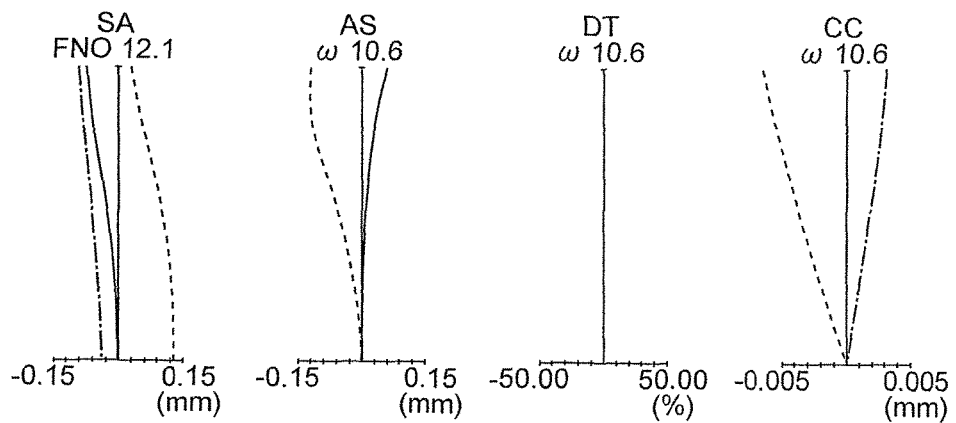

An objective optical system according to an example 8 will be described below. FIG. 16A, FIG. 16B, and FIG. 16C are lens cross-sectional views of the objective optical system according to the example 8, where, FIG. 16A is a cross-sectional view in a normal observation state, FIG. 16B is a cross-sectional view in an intermediate state, and FIG. 16C is a cross-sectional view in a proximity magnifying observation state.

The objective optical system of the example 8, as shown in FIG. 16A, FIG. 16B, and FIG. 16C, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a negative meniscus lens L3 having a convex surface directed toward the image side, a positive meniscus lens L4 having a convex surface directed toward the image side, a positive meniscus lens L5 having a convex surface directed toward the image side, a biconvex positive lens L6, and a negative meniscus lens L7 having a convex surface directed toward the image side. Here, the positive meniscus lens L2 and the negative meniscus lens L3 form a cemented lens having a positive refractive power. The biconvex positive lens L6 and the negative meniscus lens L7 form a cemented lens having a positive refractive power.

The second lens group G2 includes a biconcave negative lens L8 and a positive meniscus lens L9 having a convex surface directed toward the object side. Here, the biconcave negative lens L8 and the positive meniscus lens L9 form a cemented lens having a negative refractive power.

An aperture stop S is disposed between the first lens group G1 and the second lens group G2. More elaborately, the aperture stop S is disposed nearest to an object in the second lens group G2.

The third lens group G3 includes a biconvex positive lens L10, a biconvex positive lens L11, a biconcave negative lens L12, a planoconvex positive lens L13, and a negative meniscus lens L14 having a convex surface directed toward the image side. Here, the biconvex positive lens L11 and the planoconcave negative lens L12 form a cemented lens having a negative refractive power.

A plane-parallel plate F1 is disposed on the image side of the planoconcave negative lens L1. A plane-parallel plate F2 and a cover glass CG are disposed on the image side of the third lens group G3.

At the time of focusing, the second lens group G2 and the aperture stop S move integrally. When focusing is carried out from a state of being focused to an object point at a long distance to an object point at a close distance, the second lens group G2 and the aperture stop S move toward the image side.

The objective optical system of the example 8 has the abovementioned basic arrangement, and satisfies each of conditional expressions (1) to (15). Moreover, by letting a focal length of each lens group from the first lens group G1 to the third lens group G3 to be an appropriate value, there is no degradation of image quality, and a compact objective optical system is realized.

FIG. 17A, FIG. 17B, FIG. 17C, and FIG. 17D are aberration diagrams of a spherical aberration (SA), an astigmatism (AS), a distortion (DT), and a chromatic aberration of magnification (CC) respectively in the normal observation state of the example 8, FIG. 17E, FIG. 17F, FIG. 17G, and FIG. 17H are aberration diagrams of a spherical aberration (SA), an astigmatism (AS), a distortion (DT), and a chromatic aberration of magnification (CC) respectively in the intermediate state of the example 8, and FIG. 17I, FIG. 17J, FIG. 17K, and FIG. 17L are aberration diagrams of a spherical aberration (SA), an astigmatism (AS), a distortion (DT), and a chromatic aberration of magnification (CC) respectively in the proximity magnifying observation state of the example 8.

Numerical data of each example described above is shown below. In symbols, r denotes radius of curvature of each lens surface, d denotes a distance between respective lens surfaces, ne denotes a refractive index of each lens for e-line, vd denotes an Abbe number for each lens, Fno denotes an F number, IH denotes an image height. Moreover, focal length is a value for the e-line. More over, β denotes a lateral magnification of the overall objective optical system at a proximity magnifying observation state.

Example 1

Unit mm

Surface data

| Surface no. | r | d | ne | vd |
|---|---|---|---|---|
| 1 | ∞ | 0.302 | 1.88815 | 40.76 |
| 2 | 1.003 | 0.555 | | |
| 3 | ∞ | 0.300 | 1.51500 | 75.00 |
| 4 | ∞ | 0.120 | | |
| 5 | −122.064 | 0.675 | 1.48915 | 70.23 |
| 6 | −1.224 | 0.200 | 1.93429 | 18.90 |
| 7 | −3.077 | 0.547 | | |
| 8 | −11.322 | 0.905 | 1.49846 | 81.54 |
| 9 | −2.429 | 0.020 | | |
| 10 | −54.095 | 0.393 | 2.01169 | 28.27 |
| 11 | −3.429 | 0.017 | | |
| 12 | 3.765 | 0.550 | 1.48915 | 70.23 |
| 13 | −2.727 | 0.232 | 1.93429 | 18.90 |
| 14 | −8.953 | Variable | | |
| 15 (Stop) | ∞ | 0.030 | | |
| 16 | −4.445 | 0.200 | 1.73234 | 54.68 |
| 17 | 0.798 | 0.385 | 1.85504 | 23.78 |
| 18 | 1.582 | Variable | | |
| 19 | 5.329 | 1.000 | 1.49846 | 81.54 |
| 20 | −3.813 | 0.120 | | |
| 21 | 2.781 | 0.970 | 1.49846 | 81.54 |
| 22 | 6.791 | 0.020 | | |
| 23 | 3.530 | 1.620 | 1.48915 | 70.23 |
| 24 | −2.474 | 0.233 | 1.93429 | 18.90 |
| 25 | 9.188 | 1.730 | | |
| 26 | ∞ | 0.600 | 1.51825 | 64.14 |
| 27 | ∞ | 0.500 | 1.51825 | 64.14 |
| Image pickup surface | ∞ | | | |

Various data

| β | | −3.61 | |
|---|---|---|---|
| | normal observation state | intermediate state | proximity magnifying state |
| focal length | 1.198 | 1.550 | 1.134 |
| object distance | 11.8 | 1.88 | 0.00 |
| Fno | 6.304 | 7.292 | 10.411 |
| IH | 1.0 | 1.0 | 1.0 |
| d14 | 0.193 | 0.827 | 2.518 |
| d18 | 2.674 | 2.040 | 0.349 |

Example 2

Unit mm

Surface data

| Surface no. | r | d | ne | vd |
|---|---|---|---|---|
| 1 | ∞ | 0.304 | 1.88815 | 40.76 |
| 2 | 0.864 | 0.653 | | |
| 3 | −3.585 | 1.336 | 1.48915 | 70.23 |
| 4 | −1.273 | 0.323 | 1.85504 | 23.78 |
| 5 | −1.763 | 0.028 | | |
| 6 | ∞ | 0.833 | 1.82017 | 46.62 |
| 7 | −1.506 | 0.266 | 1.93429 | 18.90 |
| 8 | −3.218 | 0.028 | | |
| 9 | 7.321 | 0.507 | 1.88815 | 40.76 |
| 10 | −7.321 | Variable | | |
| 11 (Stop) | ∞ | 0.038 | | |
| 12 | −6.723 | 0.266 | 1.77621 | 49.60 |
| 13 | 0.926 | 0.342 | 1.93429 | 18.90 |
| 14 | 1.439 | Variable | | |
| 15 | 9.977 | 1.088 | 1.49846 | 81.54 |
| 16 | −2.696 | 0.040 | | |
| 17 | 3.251 | 1.269 | 1.48915 | 70.23 |
| 18 | −3.724 | 0.285 | 1.93429 | 18.90 |
| 19 | −24.061 | 0.200 | | |
| 20 | ∞ | 0.400 | 1.52300 | 65.13 |
| 21 | ∞ | 3.205 | | |
| 22 | ∞ | 0.650 | 1.51825 | 64.14 |
| 23 | ∞ | 0.500 | 1.51825 | 64.14 |
| Image pickup surface | ∞ | | | |

Various data

| β | | −3.75 | |
|---|---|---|---|
| | normal observation state | intermediate state | proximity magnifying state |
| focal length | 1.256 | 1.555 | 1.439 |
| object distance | 11.875 | 1.786 | 0.00 |
| Fno | 7.619 | 8.467 | 11.470 |
| IH | 1.12 | 1.12 | 1.12 |
| d10 | 0.133 | 0.587 | 1.983 |
| d14 | 2.153 | 1.699 | 0.303 |

Example 3

Unit mm

Surface data

| Surface no. | r | d | ne | vd |
|---|---|---|---|---|
| 1 | ∞ | 0.320 | 1.88815 | 40.76 |
| 2 | 0.961 | 0.875 | | |
| 3 | −12.130 | 1.383 | 1.48915 | 70.23 |
| 4 | −1.270 | 0.340 | 1.85504 | 23.78 |
| 5 | −1.829 | 0.030 | | |
| 6 | ∞ | 0.833 | 1.82017 | 46.62 |
| 7 | −1.756 | 0.280 | 1.93429 | 18.90 |
| 8 | −3.697 | 0.030 | | |
| 9 | 9.249 | 0.477 | 1.88815 | 40.76 |
| 10 | −9.249 | Variable | | |
| 11 (Stop) | ∞ | 0.040 | | |
| 12 | −10.838 | 0.280 | 1.77621 | 49.60 |
| 13 | 1.028 | 0.360 | 1.93429 | 18.90 |
| 14 | 1.651 | Variable | | |
| 15 | 4.181 | 1.078 | 1.48915 | 70.23 |
| 16 | −4.181 | 0.040 | | |
| 17 | 2.804 | 1.264 | 1.48915 | 70.23 |
| 18 | −4.605 | 0.267 | | |
| 19 | −3.184 | 0.280 | 1.93429 | 18.90 |
| 20 | ∞ | 0.100 | | |
| 21 | ∞ | 0.400 | 1.52300 | 65.13 |
| 22 | ∞ | 2.018 | | |
| 23 | ∞ | 0.700 | 1.51825 | 64.14 |
| 24 | ∞ | 0.650 | 1.51825 | 64.14 |
| Image pickup surface | ∞ | | | |

Various data

| β | | −3.53 | |
|---|---|---|---|
| | normal observation state | intermediate state | proximity magnifying state |
| focal length | 1.388 | 1.636 | 1.306 |
| object distance | 12.50 | 1.88 | 0.00 |
| Fno | 8.332 | 9.044 | 12.001 |

-continued

| Unit mm | | | |
|---|---|---|---|
| IH | 1.2 | 1.2 | 1.2 |
| d10 | 0.140 | 0.656 | 2.410 |
| d14 | 2.697 | 2.181 | 0.427 |

Example 4

| Unit mm | | | |
|---|---|---|---|
| Surface data | | | |
| Surface no. | r | d | ne | vd |
| 1 | ∞ | 0.288 | 1.88815 | 40.76 |
| 2 | 1.013 | 1.044 | | |
| 3 | 11.611 | 1.539 | 1.48915 | 70.23 |
| 4 | −1.257 | 0.216 | 1.79192 | 25.68 |
| 5 | −1.780 | 0.018 | | |
| 6 | −8.010 | 1.258 | 1.82017 | 46.62 |
| 7 | −1.582 | 0.252 | 1.93429 | 18.90 |
| 8 | −3.780 | 0.020 | | |
| 9 | 5.793 | 0.474 | 2.01169 | 28.27 |
| 10 | −13.750 | Variable | | |
| 11 (Stop) | ∞ | 0.050 | | |
| 12 | −8.531 | 0.252 | 1.77621 | 49.60 |
| 13 | 0.964 | 0.328 | 1.93429 | 18.90 |
| 14 | 1.500 | Variable | | |
| 15 | 3.475 | 1.167 | 1.48915 | 70.23 |
| 16 | −3.665 | 0.035 | | |
| 17 | 2.546 | 1.165 | 1.48915 | 70.23 |
| 18 | −5.453 | 0.204 | | |
| 19 | −3.110 | 0.252 | 1.93429 | 18.90 |
| 20 | ∞ | 0.090 | | |
| 21 | ∞ | 0.400 | 1.52300 | 65.13 |
| 22 | ∞ | 2.248 | | |
| 23 | ∞ | 0.600 | 1.51825 | 64.14 |
| 24 | ∞ | 0.550 | 1.51825 | 64.14 |
| Image pickup surface | ∞ | | | |

| Various data | | | |
|---|---|---|---|
| β | −3.15 | | |
| | normal observation state | intermediate state | proximity magnifying state |
| focal length | 1.295 | 1.587 | 1.326 |
| object distance | 11.25 | 1.80 | 0.00 |
| Fno | 7.250 | 8.128 | 10.805 |
| IH | 1.08 | 1.08 | 1.08 |
| d10 | 0.115 | 0.652 | 2.094 |
| d14 | 2.274 | 1.737 | 0.295 |

Example 5

| Unit mm | | | |
|---|---|---|---|
| Surface data | | | |
| Surface no. | r | d | ne | vd |
| 1 | ∞ | 0.3630 | 1.88815 | 40.78 |
| 2 | 0.8405 | 0.6435 | | |
| 3 | ∞ | 0.3500 | 1.51500 | 75.00 |
| 4 | ∞ | 0.4600 | | |
| 5 | −5.7803 | 0.7150 | 1.48915 | 70.23 |
| 6 | −1.2068 | 0.3400 | 1.93429 | 18.90 |
| 7 | −1.4746 | 0.0100 | | |
| 8 | 6.1041 | 0.9930 | 1.48915 | 70.23 |
| 9 | −3.0861 | 0.2200 | 1.93429 | 18.90 |
| 10 | −3.9094 | 0.0100 | | |
| 11 | 3.1818 | 1.0340 | 1.48915 | 70.23 |
| 12 | −1.8654 | 0.2000 | 1.93429 | 18.90 |
| 13 | −3.3668 | Variable | | |
| 14 (Stop) | ∞ | 0.0600 | | |
| 15 | −3.5507 | 0.2000 | 1.73234 | 54.68 |
| 16 | 0.7433 | 0.5000 | 1.85504 | 23.78 |
| 17 | 1.4107 | Variable | | |
| 18 | 3.8773 | 1.1770 | 1.49846 | 81.54 |
| 19 | −4.0709 | 0.2410 | | |
| 20 | 2.8870 | 1.1850 | 1.49846 | 81.54 |
| 21 | −4.6530 | 0.1950 | | |
| 22 | −3.2777 | 0.2000 | 1.93429 | 18.90 |
| 23 | −11.1456 | 2.4000 | | |
| 24 | ∞ | 0.7500 | 1.51825 | 64.14 |
| 25 | ∞ | 0.6500 | 1.51825 | 64.14 |
| Image pickup surface | ∞ | | | |

| Various data | | | |
|---|---|---|---|
| β | −3.58 | | |
| | normal observation state | intermediate state | proximity magnifying state |
| focal length | 1.484 | 1.729 | 1.377 |
| object distance | 14.20 | 2.12 | 0.00 |
| Fno | 5.296 | 5.729 | 7.535 |
| IH | 1.2 | 1.2 | 1.2 |
| d13 | 0.097 | 0.448 | 1.720 |
| d17 | 1.823 | 1.472 | 0.200 |

Example 6

| Unit mm | | | |
|---|---|---|---|
| Surface data | | | |
| Surface no. | r | d | ne | vd |
| 1 | ∞ | 0.270 | 1.88815 | 40.76 |
| 2 | 0.763 | 0.776 | | |
| 3 | −8.381 | 0.894 | 1.48915 | 70.23 |
| 4 | −1.052 | 0.198 | 1.69417 | 31.07 |
| 5 | −1.692 | 0.020 | | |
| 6 | −3.224 | 0.865 | 1.82017 | 46.62 |
| 7 | −1.635 | 0.233 | 1.93429 | 18.90 |
| 8 | −1.821 | 0.017 | | |
| 9 | 2.764 | 0.639 | 1.48915 | 70.23 |
| 10 | −1.778 | 0.200 | 1.85504 | 23.78 |
| 11 | −3.961 | Variable | | |
| 12 (Stop) | ∞ | 0.010 | | |
| 13 | −17.787 | 0.233 | 1.77621 | 49.60 |
| 14 | 0.893 | 0.387 | 1.85504 | 23.78 |
| 15 | 1.486 | Variable | | |
| 16 | 6.315 | 1.050 | 1.48915 | 70.23 |
| 17 | −2.706 | 0.240 | 1.93429 | 18.90 |
| 18 | −2.941 | 0.033 | | |
| 19 | 2.752 | 1.080 | 1.48915 | 70.23 |
| 20 | −8.441 | 0.239 | | |
| 21 | −4.386 | 0.230 | 1.93429 | 18.90 |
| 22 | ∞ | 0.280 | | |
| 23 | ∞ | 0.400 | 1.52300 | 65.13 |
| 24 | ∞ | 2.240 | | |
| 25 | ∞ | 0.550 | 1.51825 | 64.14 |
| 26 | ∞ | 0.550 | 1.51825 | 64.14 |
| Image pickup surface | ∞ | | | |

-continued

Unit mm

Various data

| | | |
|---|---|---|
| β | | −3.82 |

| | normal observation state | intermediate state | proximity magnifying state |
|---|---|---|---|
| focal length | 1.162 | 1.487 | 1.418 |
| object distance | 10.40 | 1.56 | 0.00 |
| Fno | 6.605 | 7.253 | 9.640 |
| IH | 1.0 | 1.0 | 1.0 |
| d11 | 0.143 | 0.659 | 2.460 |
| d15 | 2.950 | 2.434 | 0.633 |

Example 7

Unit mm

Surface data

| Surface no. | r | d | ne | vd |
|---|---|---|---|---|
| 1 | ∞ | 0.288 | 1.88815 | 40.76 |
| 2 | 0.759 | 1.359 | | |
| 3 | −2.066 | 0.420 | 1.77621 | 49.60 |
| 4 | −1.396 | 0.017 | | |
| 5 | −6.532 | 0.934 | 1.82017 | 46.62 |
| 6 | −1.466 | 0.252 | 1.93429 | 18.90 |
| 7 | −2.369 | 0.018 | | |
| 8 | 3.893 | 0.514 | 1.48915 | 70.23 |
| 9 | −2.293 | 0.216 | 1.85504 | 23.78 |
| 10 | −3.873 | Variable | | |
| 11 (Stop) | ∞ | 0.030 | | |
| 12 | −7.033 | 0.252 | 1.77621 | 49.60 |
| 13 | 0.945 | 0.420 | 1.85504 | 23.78 |
| 14 | 1.903 | 0.019 | | |
| 15 | 0.966 | 0.194 | 1.85504 | 23.78 |
| 16 | 0.834 | Variable | | |
| 17 | 26.076 | 0.817 | 1.48915 | 70.23 |
| 18 | −2.266 | 0.036 | | |
| 19 | 2.593 | 1.035 | 1.48915 | 70.23 |
| 20 | −6.934 | 0.211 | | |
| 21 | −4.254 | 0.252 | 1.93429 | 18.90 |
| 22 | ∞ | 0.270 | | |
| 23 | ∞ | 0.400 | 1.51564 | 75.00 |
| 24 | ∞ | 2.433 | | |
| 25 | ∞ | 0.600 | 1.51825 | 64.14 |
| 26 | ∞ | 0.550 | 1.51825 | 64.14 |
| Image pickup surface | ∞ | | | |

Various data

| | | |
|---|---|---|
| β | | −4.17 |

| | normal observation state | intermediate state | proximity magnifying state |
|---|---|---|---|
| focal length | 1.238 | 1.548 | 1.230 |
| object distance | 11.25 | 1.75 | 0.00 |
| Fno | 7.632 | 8.500 | 12.024 |
| IH | 1.08 | 1.08 | 1.08 |
| d10 | 0.135 | 0.631 | 2.280 |
| d16 | 2.431 | 1.935 | 0.286 |

Example 8

Unit mm

Surface data

| Surface no. | r | d | ne | vd |
|---|---|---|---|---|
| 1 | ∞ | 0.290 | 1.88815 | 40.76 |
| 2 | 0.710 | 0.757 | | |
| 3 | ∞ | 0.300 | 1.51564 | 75.00 |
| 4 | ∞ | 0.170 | | |
| 5 | −3.133 | 0.580 | 1.48915 | 70.23 |
| 6 | −1.185 | 0.220 | 1.93429 | 18.90 |
| 7 | −1.584 | 0.018 | | |
| 8 | −5.481 | 0.559 | 1.48915 | 70.23 |
| 9 | −1.793 | 0.015 | | |
| 10 | −4.897 | 0.320 | 2.01169 | 28.27 |
| 11 | −3.562 | 0.016 | | |
| 12 | 3.210 | 0.761 | 1.48915 | 70.23 |
| 13 | −1.765 | 0.200 | 1.93429 | 18.90 |
| 14 | −2.862 | Variable | | |
| 15 (Stop) | ∞ | 0.030 | | |
| 16 | −3.896 | 0.192 | 1.73234 | 54.68 |
| 17 | 0.792 | 0.284 | 1.85504 | 23.78 |
| 18 | 1.465 | Variable | | |
| 19 | 3.675 | 0.860 | 1.48915 | 70.23 |
| 20 | −3.556 | 0.016 | | |
| 21 | 7.274 | 0.601 | 1.58566 | 46.42 |
| 22 | −7.541 | 0.180 | 1.85504 | 23.78 |
| 23 | 8.855 | 0.012 | | |
| 24 | 2.863 | 0.871 | 1.48915 | 70.23 |
| 25 | −9.990 | 0.691 | | |
| 26 | −2.105 | 0.240 | 1.93429 | 18.90 |
| 27 | −2.921 | 2.674 | | |
| 28 | ∞ | 0.600 | 1.51825 | 64.14 |
| 29 | ∞ | 0.520 | 1.51825 | 64.14 |
| Image pickup surface | ∞ | | | |

Various data

| | | |
|---|---|---|
| β | | −4.24 |

| | normal observation state | intermediate state | proximity magnifying state |
|---|---|---|---|
| focal length | 1.146 | 1.458 | 1.221 |
| object distance | 11.33 | 1.80 | 0.00 |
| Fno | 7.441 | 8.461 | 12.088 |
| IH | 0.98 | 0.98 | 0.98 |
| d14 | 0.149 | 0.636 | 2.099 |
| d18 | 2.072 | 1.585 | 0.122 |

Next, the values of conditional expressions (1) to (15) in each example of the objective optical system are shown below.

| Conditional expression | Example 1 | Example 2 | Example 3 | Example 4 |
|---|---|---|---|---|
| (1) $f_f/f_e$ | 0.28 | 0.27 | 0.28 | 0.32 |
| (2) $|β|$ | 3.61 | 3.75 | 3.53 | 3.15 |
| (3) ω | 65.81 | 65.13 | 66.23 | 65.79 |
| (4) $f_{G12w}/f_w$ | −1.40 | −1.29 | −1.84 | −1.43 |
| (5) $f_{G12e}/f_e$ | 1.49 | 1.25 | 1.32 | 1.57 |
| (6) $f_{G1L2}/f_w$ | 2.11 | 2.70 | 2.01 | 1.86 |
| (7) $HF/f_e$ | 1.28 | 1.27 | 1.28 | 1.32 |
| (8) $f_{G1L4}/f_w$ | 3.01 | 3.34 | 3.80 | 3.15 |
| (9) $f_{G1}/f_{G2}$ | −0.61 | −0.56 | −0.54 | −0.58 |
| (10) $f_{G2}/f_{G3}$ | −0.66 | −0.53 | −0.64 | −0.63 |
| (11) $EN_w/EN_e$ | 0.24 | 0.31 | 0.26 | 0.31 |
| (12) $EN_w/f_w$ | 0.39 | 0.33 | 0.32 | 0.37 |
| (13) $R_{3GLi}/f_e$ | −2.18 | −2.59 | −2.44 | −2.35 |

-continued

| | | | | |
|---|---|---|---|---|
| (14) $f_{G2}/f_w$ | -1.49 | -1.34 | -1.50 | -1.41 |
| (15) $\Delta_{2G}/LTL$ | 0.15 | 0.12 | 0.15 | 0.13 |
| Conditional expression | Example 5 | Example 6 | Example 7 | Example 8 |
| (1) $f_f/f_e$ | 0.28 | 0.26 | 0.24 | 0.24 |
| (2) $|\beta|$ | 3.58 | 3.82 | 4.17 | 4.24 |
| (3) $\omega$ | 64.97 | 66.77 | 65.65 | 65.90 |
| (4) $f_{G12w}/f_w$ | -1.46 | -1.85 | -1.51 | -1.13 |
| (5) $f_{G12e}/f_e$ | 1.11 | 0.93 | 1.10 | 1.36 |
| (6) $f_{G1L2}/f_w$ | 2.00 | 2.03 | 3.52 | 3.10 |
| (7) $HF/f_e$ | 1.28 | 1.26 | 1.24 | 1.24 |
| (8) $f_{G1L4}/f_w$ | 3.54 | 4.61 | 4.37 | 10.06 |
| (9) $f_{G1}/f_{G2}$ | -0.64 | -0.53 | -0.57 | -0.56 |
| (10) $f_{G2}/f_{G3}$ | -0.52 | -0.59 | -0.58 | -0.55 |
| (11) $EN_w/EN_e$ | 0.29 | 0.21 | 0.26 | 0.28 |
| (12) $EN_w/f_w$ | 0.32 | 0.31 | 0.31 | 0.32 |
| (13) $R_{3GLi}/f_e$ | -2.38 | -3.09 | -3.46 | -1.72 |
| (14) $f_{G2}/f_w$ | -1.02 | -1.63 | -1.39 | -1.39 |
| (15) $\Delta_{2G}/LTL$ | 0.11 | 0.16 | 0.15 | 0.14 |

Various embodiments of the present invention have been described heretofore. However, the present invention is not limited only to the embodiments described above, and embodiments in which arrangements of these embodiments have been combined appropriately without departing from the scope of the invention are also within the scope of the present invention.

(Appended Mode)

The present invention also includes the following inventions which are conceived form abovementioned embodiments and examples.

(Appended Mode 1)

An objective optical system, comprising in order from an object side;

a first lens group having a positive refractive power, a second lens group having a negative refractive power, and a third lens group having a positive refractive power, wherein focusing is carried out by moving the second lens group with respect to a change in an object-point distance, and the following condition expression (1) is satisfied:

$$0 \leq f_f/f_e < 0.33 \quad (1),$$

where, $f_f$ denotes a front focal position at the time of focusing to an object point at a close distance, and $f_e$ denotes a focal length of the overall objective optical system at the time of focusing to the object point at the close distance.

(Appended Mode 2)

An objective optical system, comprising in order from an object side;

a first lens group having a positive refractive power, a second lens group having a negative refractive power, and a third lens group having a positive refractive power, wherein focusing is carried out by moving the second lens group with respect to a change in an object-point distance, and the following conditional expressions (2) and (3) are satisfied:

$$3 < |\beta| \quad (2), \text{ and}$$

$$60° < \omega \quad (3),$$

where, $\beta$ denotes a lateral magnification of the overall objective optical system at the time of focusing to an object point at a close distance, and $\omega$ denotes the maximum half angle of view at the time of focusing to an object point at a long distance.

(Appended Mode 3)

An objective optical system, comprising in order from an object side;

a first lens group having a positive refractive power, a second lens group having a negative refractive power, and a third lens group having a positive refractive power, wherein focusing is carried out by moving only the second lens group with respect to a change in an object-point distance, and the first lens group includes at least one negative lens, two cemented lenses, and one positive lens, and the negative lens is disposed nearest to an object, and the cemented lens includes a positive lens and a negative lens.

(Appended Mode 4)

The objective optical system according to any one of Appended Modes 1 to 3, wherein the objective optical system is used for an endoscope.

(Appended Mode 5)

The objective optical system according to any one of Appended Modes 1 to 3, wherein the following conditional expressions (4) and (5) are satisfied:

$$-2 < f_{G12w}/f_w < -1 \quad (4), \text{ and}$$

$$0.5 < f_{G12e}/f_e < 1.62 \quad (5),$$

where, $f_{G12w}$ denotes a combined focal length of the first lens group and the second lens group at the time of focusing to the object point at the long distance, $f_{G12e}$ denotes a combined focal length of the first lens group and the second lens group at the time of focusing to the object point the a close distance, $f_e$ denotes a focal length of the overall objective optical system at the time of focusing to then object point at the long distance, and $f_w$ denotes the focal length of the overall objective optical system at the time of focusing to the object point at the close distance.

(Appended Mode 6)

The objective optical system according to any one of Appended Modes 1 to 5, wherein
the following conditional expression (6), (7) are satisfied:

$$1.81 < f_{G1L2}/f_w < 3.85 \quad (6), \text{ and}$$

$$0.9 < HF/f_e < 1.33 \quad (7),$$

where, $f_{G1L2}$ denotes a focal length of a lens alone, positioned second from the object side in the first lens group, $f_w$ denotes the focal length of the overall objective optical system at the time of focusing to the object point at the long distance, HF denotes a front principal-point position at the time of focusing to the object point at the close distance, and $f_e$ denotes the focal length of the overall objective optical system at the time of focusing to the object point at the close distance.

(Appended Mode 7)

The objective optical system according to any one of Appended Modes 1 to 5, wherein the following conditional expression (8), (9), (10), (11) and (12) are satisfied:

$$2.5 < f_{G1L4}/f_w < 10.5 \quad (8),$$

$$-0.65 < f_{G1}/f_{G2} < -0.52 \quad (9),$$

$$-0.68 < f_{G2}/f_{G3} < -0.49 \quad (10),$$

$$0.2 < EN_w/EN_e < 0.34 \quad (11), \text{ and}$$

$$0.28 < EN_w/f_w < 0.43 \quad (12),$$

where, $f_{G1L4}$ denotes a focal length of a lens component positioned fourth from the object side in the first lens group, $f_w$ denotes the focal length of the overall objective optical system at the time of focusing to the object point at the long distance, $f_{G1}$ denotes a focal length of the first lens group, $f_{G2}$ denotes the focal length of the second lens group, $f_{G3}$ denotes a focal length of the third lens group, $EN_w$ denotes a most diagonal entrance-pupil position at the time of focusing to the object point at the long distance, $EN_e$ denotes a most diagonal entrance-pupil position at the time of focusing to the object point at the close distance, and here the lens component is either a single lens or a cemented lens.

(Appended Mode 8)

The objective optical system according to any one of Appended Modes 1 to 5, wherein the following conditional expression (13), (14), and (15) are satisfied:

$$-6 < R_{3GLi}/f_e < -1.7 \quad (13),$$

$$-1.7 < f_{G2}/f_w < -1.3 \quad (14)$$

$$0.1 < \Delta_{2G}/LTL < 0.17 \quad (15),$$

where, $R_{3GLi}$ denotes a radius of curvature on the object side of a lens positioned nearest to an image in the third lens group, $f_e$ denotes the focal length of the objective optical system at the time of focusing to the object point at the close distance, $f_{G2}$ denotes the focal length of the second lens group, fw denotes the focal length of the overall objective optical system at the time of focusing to the object point at the long distance, $\Delta_{2G}$ denotes an amount of movement of the second lens group when focused from the object point at the long distance to the object point at the close distance, and LTL denotes a overall length of the objective optical system.

An objective optical system according to an embodiment of the present invention shows an effect that the objective optical system is small-sized and with a large magnification at the time of proximity magnifying observation and macro photography, and has a high resolving power, while enabling to change an object-point distance to which the focusing can be done.

As described heretofore, the present invention is useful for an objective optical system in which the objective optical system is small-sized and with a large magnification at the time of proximity magnifying observation and macro photography, and has a high resolving power, while enabling to change an object-point distance to which the focusing can be done.

What is claimed is:

1. An objective optical system comprising, in order from an object side:

a first lens group having a positive refractive power, a second lens group having a negative refractive power, and a third lens group having a positive refractive power, wherein:

focusing is carried out by moving only the second lens group with respect to a change in an object-point distance, the first lens group includes at least one negative lens, two cemented lenses, and one positive lens, the negative lens is disposed nearest to an object, both of the two cemented lenses include, in order from the object side, a positive lens and a negative lens, and the following conditional expression (8) is satisfied:

$$2.5 < f_{G1L4}/f_w < 10.5 \quad (8),$$

where:

$f_{G1L4}$ denotes a focal length of a lens component positioned fourth from the object side in the first lens group, and $f_w$ denotes a focal length of the overall objective optical system at a time of focusing to an object point at a long distance.

2. The objective optical system according to claim 1, wherein the following conditional expression (9) is satisfied:

$$-0.65 < f_{G1}/f_{G2} < -0.52 \quad (9),$$

where:

$f_{G1}$ denotes a focal length of the first lens group, and $f_{G2}$ denotes a focal length of the second lens group.

3. The objective optical system according to claim 1, wherein the following conditional expression (10) is satisfied:

$$-0.68 < f_{G2}/f_{G3} < -0.49 \quad (10),$$

where:

$f_{G2}$ denotes a focal length of the second lens group, and $f_{G3}$ denotes a focal length of the third lens group.

4. An objective optical system comprising, in order from an object side:

a first lens group having a positive refractive power, a second lens group having a negative refractive power, and a third lens group having a positive refractive power, wherein:

focusing is carried out by moving the second lens group with respect to a change in an object-point distance, the following conditional expressions (2), (3), and (8) are satisfied:

$$3 < |\beta| \quad (2),$$

$$60° < \omega \quad (3), \text{ and}$$

$$2.5 < f_{G1L4}/f_w < 10.5 \quad (8),$$

where:

$\beta$ denotes a lateral magnification of the overall objective optical system at a time of focusing to an object point at a close distance, $\omega$ denotes a maximum half angle of view at a time of focusing to an object point at a long distance, $f_{G1L4}$ denotes a focal length of a lens component positioned fourth from the object side in the first lens group, and $f_w$ denotes a focal length of the overall objective optical system at the time of focusing to the object point at the long distance.

5. An objective optical system comprising, in order from an object side:

a first lens group having a positive refractive power, a second lens group having a negative refractive power, and a third lens group having a positive refractive power, wherein:

focusing is carried out by moving the second lens group with respect to a change in an object-point distance, the following conditional expressions (2), (3), and (9) are satisfied:

$$3<|\beta| \qquad (2),$$

$$60°<\omega \qquad (3), \text{ and}$$

$$-0.65<f_{G1}/f_{G2}<-0.52 \qquad (9),$$

where:

β denotes a lateral magnification of the overall objective optical system at a time of focusing to an object point at a close distance, ω denotes a maximum half angle of view at a time of focusing to an object point at a long distance, $f_{G1}$ denotes a focal length of the first lens group, and $f_{G2}$ denotes a focal length of the second lens group.

6. An objective optical system comprising, in order from an object side:

a first lens group having a positive refractive power, a second lens group having a negative refractive power, and a third lens group having a positive refractive power, wherein:

focusing is carried out by moving the second lens group with respect to a change in an object-point distance, the following conditional expressions (2), (3), and (10) are satisfied:

$$3<|\beta| \qquad (2),$$

$$60°<\omega \qquad (3), \text{ and}$$

$$-0.68<f_{G2}/f_{G3}<-0.49 \qquad (10),$$

where:

β denotes a lateral magnification of the overall objective optical system at a time of focusing to an object point at a close distance, ω denotes a maximum half angle of view at a time of focusing to an object point at a long distance, $f_{G2}$ denotes a focal length of the second lens group, and $f_{G3}$ denotes a focal length of the third lens group.

\* \* \* \* \*